United States Patent [19]
Ellis et al.

[11] Patent Number: 4,960,690
[45] Date of Patent: Oct. 2, 1990

[54] NUCLEIC ACID PROBES FOR PRENATAL SEXING

[75] Inventors: Steven B. Ellis, La Jolla; Michael M. Harpold, San Diego, both of Calif.

[73] Assignee: The Salk Institute Biotechnology Industrial Associates, Inc., San Diego, Calif.

[21] Appl. No.: 871,111

[22] Filed: Jun. 5, 1986

Related U.S. Application Data

[63] Continuation-in-part of Ser. No. 739,817, May 31, 1985, Pat. No. 4,769,319.

[51] Int. Cl.$^5$ ........................ C12Q 1/68; C07H 15/12
[52] U.S. Cl. ..................................... 435/6; 435/172.3; 436/501; 436/814; 536/27; 935/3; 935/9; 935/63; 935/78
[58] Field of Search ................ 435/6, 172.3; 436/501, 436/814; 536/27; 935/3, 9, 63, 78

[56] References Cited
FOREIGN PATENT DOCUMENTS
8600342 1/1986 World Int. Prop. O. .

OTHER PUBLICATIONS

Nallaseth, F. S. et al., "Isolation of Recombinant . . . Male-Specific Mouse DNA", Mol. Gen. Genet 190, 80–84 (1983).
Gosden, J. R. et al., "Rapid Fetal Sex Determination . . ." The Lancet 1, 540–541, Mar. 10, 1984.
Burns, J. et al., "Sensitive System for Visualizing . . ." J. Clin. Pathol 38, 1085–1092 (1985).
Bishop et al., "Single Copy DNA Sequences Specific for the Human Y Chromosome", Nature 303, 831–832 (1983).
Kunkel et al., "Organization and Heterogeneity of Sequences", Biochemistry 18, 3343–3353 (1979).
Langer, P. R. et al., "Enzymatic Synthesis of Biotive-Labeled Polynucleatides . . .", Proc. Natl. Acad. Sci. U.S.A. 78(11), 6633–6637 (Nov., 1981).
Lamar et al., "Y-encoded Species-Specific DNA in Mice . . .", Cell 37, 171–177 (1984).

Primary Examiner—Robert J. Warden
Assistant Examiner—Richard Wagner
Attorney, Agent, or Firm—Fitch, Even, Tabin & Flannery

[57] ABSTRACT

Nucleic acid hybridizaiton probes are provided which have sequences complementary to sequences of segments in bovine male-specific DNA and are suitable for sexing bovine embryos at the time of embryo transfer with nearly 100% accuracy.

33 Claims, 4 Drawing Sheets

FIGURE 1 - A

```
     SmaI
                                                                480
...CCCGGGAACA TCATCCTGAG CGCGCCTCTC AGTGCCTGCC CCGAAGCAGG CTGGGTCCTT
   420
                                XhoI
                                                                540
   CCCATGTTCA AGCCCCGAGA AGCACTCTCG AGCCCACATC GGGTTCCCTG CCGTCAATCA

600
   GGCTAGGTCC TACCCTTGGA CCGACCCCCG GCAAGCACTC CTGAGCGTGC CTCGGTCGCT

660
   GCCTCAATGG GGCGGTGCAC GGCANNNNNN NNNNNCCCTG ACAACANTCC TGAGCCAACA

716
   CCTCGGTCCC TGCACGGGAC GAGGCAGGGG CCCACCCGGC GTGAGTCCCC GACAGA...

1089                                                         1148
...GGTAGAGCCC GCATCTCGGT CCCCGCGGTG AACCTGGCCG GGTTCCTACC CcagtCAAAT
                                                          *
                                                                1208
   ACTCCTGAAG CTGCATCTCG GTCCCTGCCC TGAACCGGTC TAGGTCTAGC CCTTGTTCGG

1268
   GACGCACATC ACAGGCTCCT GAGCCCCCAT CTCTGTGCCT GCCCTGAAGG AGGCTTGGTC

NarI
                                                                1328
   CCGCCCACGG CCCGGCGCCN ACAAACACCC CTGAGCCCAC CGCCCGGTGC CTGCATTGAA

1388
   CCAGGCTGGC TCCTGCCCTC AGGCAAGACC CGGACAAACA CTCCTGAGCC CACCGCCCCG

1448
   TGCCTGCACT GAACCAGGCT GCCCCCCTCC CTAGGGCAAG ACCCTGACAA ACACTCCTGT

SmaI
                                                                1508
   GACCTCCCCG GGTCTCGCAC TGAAGCAGGC TGGCTCCTGC CTTCGTGCAA GCACCTGGCA

1568
   AAGTAACCAC CGGGAGACTC CAGCTCGCTC CGTGCCCGTC CACGTCGCTG TGTCCTGCCT

1628
   TTGGTCCCTC GCCGGGACAA AGCCCTGATC CCGCAACTCA CTCCCGGCTC TGAACCCGCA

1688
   ACgcggggCT TGGCTGCTTC AANACCCCGA GAAATGCATG TCGGTCGGCG CACTGAAGAA
   *
                                                        PvuII
                                                                1747
   GCAGTTTAGG GCCTGCNTTC TTCGNTTCTC GTGACACACA CTCCTGANCA CAGCTGCGT...

2540                                                         2600
...GGGGCCTCCC CTCCTCCACA NCGCCACCCA ACGCCCTGNG CCAACATCTC CTTCCCTGCC

* 2660
   CCGGCCAGGG CTCCNGCAAG CAATTGCCGA ACCACCNGGC AAATGCGCCT GTGCgccccc

2720
   TCGGGGCTG CACTGAACCA GTCGAGGTTC TGCCCTTGGG AGCTACCTCA ACACGTCCTC

2780
   CTGAGGCCTC CTCTCGCACT CTGCCCTGAA GCCGTGCGCG TCCTGCCCTC GATCAGACCT

2840
   CGAGAAACCC TCCTGAGGGA GCATCTCGGT CCCCGCACAG AGACAGGGTG GGCCGTGCCC
```

FIGURE 1 - B

```
           SmaI                                                   2900
TCGTTCAGTC ACCCGGGAAA CACTGCTGAG CCCGCATCTT GATCCCCGCG CTAAACCTGG

2960
CCGGGGTCCT ACCCCCAGGA AATACTCCTG AAGCAGCATC TCTGTCCCTG CCCTGAACCG

3020
GTCTAGGTCT GGCCCTTGTT CGATTCACTC AGCACAGACT CCTGAGCCCC CATCTCTGTG

3080
TCTGCCCTGA AGGAGGCTGG GTCCTGCCCA TGCCCGGCGC CGACAGACAC TCCTGAGACC
           SmaI
                                                                  3140
ACCGCCCGGG GCCTGCCCTG AACCAGGCTG GTCCCTGCCC TCGGGCAAGA CCCTGACAAA

3200
CACTCCTGAG CCCACCGCCC GGTGCCTGCT CTAAACCAGG CTGGCTCCTG CCCTCGGGCA

3260
ATACCATGAC AAACACTCCT GGGCCCCCCG CCCGGTGTCT GCACTGATCC AGGCTGGCTC

BamHI
                                                                  3320
CTGCCCTCGG TCAAGACCCT GGCAAACACT CCAGAGCCCA CTCCGGATCC CTGCACCGAA

3380
GCAGGCTGGC TCCTGCCTTC GNTCAAGCAC CTGGCAAAGT AACCGCCGGG AGACTCCAGC

3440
TCGCTCCCTG CCCGTCCACT TCGNTGTGTC CTGCATTTGG TCCCTCTCCG GGACAAAGCT

3500
GTGATCCCGC AGCTCANTCC CGGCACTGAA GCCACCTCTG GGGCTTGGCC TGCTTCAAGA

3560
CCCCGAGAAA TACATCTCGG TCGGCGCACT GAAGAAGCAG TCTAGGGCCT GCCTTCTTCG ...

EcoRI
                                                                  4060
...GAATTCGGAT GGATGCTGCC CTTGGGCAAC ACCCCCACCG CCCCCAAACT CACACAAAAC
   4000
                      SacI
                                                                  4120
ACTCCTGAGC GTTCATCTCG GTCCCTGAGC TCAACCACGG TGGTTTCTGC CTCTGGCCAA

4180
GGCCCTCGAC AATCAATCCT GAGCCCAAAC CTGGCCCCCT GGCCCTGAAC GACGGTGAGT

4240
CCTCCCCTTG TTCAAACGCC CGGAATCATT GCTGCGCCCT CATCTCACGC GCTGCACTAA

4300
ACCACGCAGA GTTCCGCCCT TCCTGAAGTG CCCGTCTAAA GTCCTGGGCC CCGTCTCGGT

4360
CACTGAACTG AACCAGTCGA GGTCCTGCCC TTTGTGCGGG CCCCTAGCAC AGACTCCCGA
                     PstI                                         4420
CCCAAACCTC TCGGTCCCTG CAGTCAAGCA ggcgttCTTT GGACTTTCCA TGTTCGAGTC SmaI
                                                                  4480
CCGGGAACAT CATCCTGAGC GCGCCTCTCA GTGCCTGCCC CGAAGCAGGC TGGGTCCTTC

4540
CCATGTTCAA GCCCCGAGAA GCACTCTCGA GCCCACATCG GGTTCCCTGC CCTCAATCAG
```

FIGURE 1 - C

```
                                                                 4600
GCTAGGTCCT ACCCTTGGAC CGACCCCCGG CAAGCACTCC TGAGCCTGCC TCGGTCGCTC

4660
CCTCAATTGG GCGGTGCACG GCATTCTTCC CGACCCTGAC AACACTCCTG AGCCAACACC

**                 4720
TCGGTCCCTG CACGGGACGA GGCTGGGTCC CACCCGGCGT cagtccccg acagacccgc 4780
ctgagcctgc tcgcggccac ggcacgcacc taggctgggg cctccgttgg gcactgtgcc 4840
gtgcaacgcc cctgagtcaa catctccttc cctgcccggg CCAGGGCTCC GGCAAGCAAT 4900
TGCCGAAGCC ACCGGCAAAT GCGCCTGTgc gcccctCGGG CGCTGCACTG AACCAGTCGA

4960
GGTTCTGCCC TTGGGAGCTA CCTCAAGACG TCCTCCTGAG GCCTCCTCTC GCACTCTGCC

5020
CTGAAGCCGT GCGCGTCCTG CCCACGATCA GACCTCGAGA AACCCTCCTG AGGGAGCATC

SmaI
                                                                 5080
TCGGTCCCCG CACAGAGACA GGGTGGCCGT GCCCTCGTTC AGTCACCCGG GAAACACTGC

5140
TGAGCCCGCA TCTTGATCCC CGCGCTAAAC CTGGCCGGGG TCCTACCCCC AGGAAATACT

5200
CCTGAAGCAG CATCTCTGTC CCTGCCCTGA ACCGGTCTAG GTCTGGCCCT TGTTCGATTC

5260
ACTCAGCACA GACTCCTGAG CCCCATCTC TGTGTCTGCC CTGAAGGAGG CTGGGTCCTG

SmaI
                                                                 5320
CCCATGCCCG GCGCCGACAG ACACTCCTGA GACCACCGCC CGGGGCCTGC CCTGAACCAG

5380
GCTGGTCCCT GCCCTCGGGC AAGACCCTGA CAAACACTCC TGAGCCCACC GCCCGGTGCC

5440
TGCTCTAAAC CAGGCTGGCT CCTGCCCTCG GCAATACCA TGACAAACAC TCCTGGGCCC

5500
CCCGCCCGGT GTCTGCACTG ATCCAGGCTG GCTCCTGCCC TCGGTCAAGA CCCTGGCAAA

BamHI
                                                                 5560
CACTCCAGAG CCCACTCCGG ATCCCTGCAC CGAAGCAGGC TGGCTCCTGC CTTCGTTCAA

5620
GCACCTGGCA AAGTAACCGC CGGGAGACTC CAGCTCGCTC CCTGCCCGTC CACTTCGCTG

5680
TGTCCTGCAT TTGGTCCCTC TCCGGGACAA AGCTGTGATC CCGCAGCTCA CTCCCGGCAC

5740
TGAAGCCACC TCTGGGGCTT GGCCTGCTTC AAGACCCCGA GAAATACATC TCGGTCGGCG

5800
CACTGAAGAA GCAGTCTAGG GCCTGCCTTC TTCGATTCCC GCGACACACA CTCCTGAGCC
```

FIGURE 1 - D

```
 PvuII
ACAGCTGCGT GCGCGCCCTG AACTCGGATG GATGCTGCCC TTGGGCAACC CCCCCACCCT
                                                             5860

SacI
                                                             5920
CCTCCCCCCA CCAAACACAC AAACACTCCT GAGCGTTCAT CTCGGTCCCT GAGCTCAACC

5980
ACGGTGGTTC CTGCCTCTGG CCAAGGCCCC CGACAAACAA TCCTGAGCCC AAACCTGGCC

6040
CCCTGGCCCC CTGGCCCCGA ACAATGGTGA GTCCTCCCCT TGTTCCAACC CCCCGGAATC

6100
ACTGCTGTGC CCTCATCTCA CGCGCTGAAC TAAACCAAGC ACGGTCGTGC CCTTCCAGAA

6160
GAGCCCGTCT AAATTCCTGA GCCCCGTCTC GGTCACTGAA CGGAACCAGT CGAGGTCCTG

EcoRI adapter    6203
CCCTTGTGCG AGCGCCTAGT CCTTGACCGT AAGACATGAA TTC.....
```

NUCLEIC ACID PROBES FOR PRENATAL SEXING

This application is a continuation-in-part of Application Ser. No. 739,817, filed May 31, 1985, now U.S. Pat. No. 4,769,319.

TECHNICAL FIELD

The present invention relates to prenatal sexing of mammals. More particularly, it relates to nucleic acid hybridization probes useful for such sexing.

BACKGROUND OF THE INVENTION

The capability to determine soon after fertilization, with nearly 100% accuracy, the sex of mammalian embryos would provide numerous advantages in the dairy and livestock industries as well as veterinary and human medicine. The economic efficiency of livestock and dairy operations would be significantly improved by allowing gestation to continue beyond the very early stage only for embryos of the desired sex. Certain diseases, such as X-chromosome-linked diseases in humans and comparable diseases in other mammals, affect individuals of only one sex; an early, nearly certain determination of the sex of an embryo which, if carried to term, might be an individual with such a disease would provide valuable information on which to base a decision whether or not to carry the embryo to term.

In situations where, for economic or health reasons, a determination of embryo sex is indicated, it is advantageous to determine the sex as soon as possible after fertilization. Risks, to the life and health of a female carrying an embryo, of having the embryo aborted increase substantially as the period of gestation lengthens. With livestock, it is economically inefficient, both because of risks to life and health and because of reduced reproductive efficiency, for a female to carry longer than necessary an embryo that ultimately will be aborted.

With recent advances in in vitro fertilization, long-term embryo-preservation and embryo-transfer technologies, it would be feasible to avoid all risks and costs associated with pregnancy and abortion of an embryo of undesired sex, if it were possible to determine highly accurately the sex of an in vitro fertilized or transferred embryo prior to or at the time transfer for gestation to term is carried out. See, e.g., King and Picard, "Sexing Cattle Embryos: An Update," in Proc. Ann. Conf. on Artificial Insemination and Embryo-Transfer, 1986, pp. 35-39.

Prior to the present invention, a sufficiently sensitive, rapid and reliable method, employing nucleic acid hybridization probes, for determining the sex of a mammalian embryo of fewer than about $10^4$ cells in three or fewer days has not been available. Thus, until the instant invention, it has not been possible, employing nucleic acid probes, to realize the many health and economic benefits of sexing embryos, with near certainty, soon after fertilization.

Human fetuses have been sexed, at 6 to 15 weeks gestational age, by nucleic acid hybridization of DNA from cells obtained from chorion or placental biopsy or embryonic fluid. In these fetal sex determinations, probes were used that correspond to DNA segments that occur about $10^3$ times in male human DNA and much more frequently in male than female human DNA. Vergnaud et al., Patent Cooperation Treaty Application Publication No. 86/00342; Vergnaud et al., Brit. Med. J. 289, 73-76 (1984); Lau et al., The Lancet, Jan. 7, 1984, pp. 14-16; Gosden et al., The Lancet, Dec. 25, 1982, pp. 1416-1419; Bostock et al., Nature 272, 324 (1978). Probes of the present invention, which are sufficiently sensitive to sex a mammal with DNA from fewer than $10^3$ of its cells, can also be used to sex fetuses.

DNA segments that preferentially hybridize to male, in comparison with female, human DNA have been found. See Kunkel et al., Science 191, 1189-1190 (1976); Cooke, Nature 262, 182 (1976); Bostock et al., supra; Gosden et al., supra; and Bishop et al., Nature 303, 831 (1983). The sequences of these segments are not known. The extent to which any of these segments preferentially hybridizes to male (in comparison with female) DNA of non-human species has not been tested and, hence, remains unknown. There is no segment that is known to bind preferentially to male, in comparison with female, DNA of species of genera Bos (bovine), Capra (caprine), Equus (equine), Ovis (ovine), and Sus (porcine).

Further, there is nothing in the prior art to indicate that any DNA segments exist in mammalian male DNA that could be used to provide the basis for a nucleic acid probe to sex by nucleic acid hybridization, in less than a few 3 days and with nearly 100% accuracy, a mammalian embryo at an early stage, at or before the time of transfer of the embryo for gestation to term.

SUMMARY OF THE INVENTION

We have discovered segments in male bovine DNA that make feasible the rapid, nearly 100% accurate sexing of bovine embryos by nucleic acid hybridization with an amount of DNA equal to the amount obtained from as few as about 4 embryonic cells.

We have found nucleic acid probes which can be employed to sex bovine embryos in less than a few days at an early stage, at or before the time embryo transfer is carried out.

With the present invention, the advantages of very early and highly accurate sexing of bovine embryos can be realized.

Further, we have discovered methods for isolating, from male DNA of a mammalian species, segments which hybridize to a significantly greater extent with the DNA of the male than of the female of the species. Such segments are the basis for nucleic acid hybridization probes for sexing mammalian embryos and fetuses.

DETAILED DESCRIPTION OF INVENTION

The present invention encompasses nucleic acids which, when suitably labeled to be detectable in an hybridization system, are hybridization probes useful for sexing mammals prenatally; the probes resulting from so labeling such nucleic acids; methods of isolating and identifying such nucleic acids and probes; and methods of using the probes in prenatal sexing of mammals.

The nucleic acids of the invention, both unlabeled and labeled (i.e., probes), can be single-stranded or double-stranded DNA or RNA or hybrids between DNA and RNA. The sequence of a labeled nucleic acid is the sequence the nucleic acid would have if each labeled nucleotide (i.e., deoxyribonucleotide or ribonucleotide) in the sequence were replaced with the corresponding unlabeled nucleotide. Thus, if a DNA is labeled with biotin linked to the 5-position of deoxyuridylate residues, the sequence of the labeled DNA is the same as that of the DNA wherein all of the biotin-labeled deoxyuridylates are replaced with thymidylates. The sequences of a DNA and a RNA are the same if every deoxyribonucleotide, except thymidylate, in the DNA is replaced with the corresponding ribonucleotide in the RNA and every thymidylate in the DNA is replaced with uridylate in the RNA.

The essential feature of the nucleic acids of the invention, both unlabeled and labeled, is that, when in single-stranded form, they hybridize to a significantly greater extent with total male DNA than total female DNA of a bovine species, when the hybridizations are carried out under substantially the same conditions. By hybridization to a "significantly greater extent" is meant that the quantity of nucleic acid that hybridizes is, with a probability greater than 0.99, larger.

The preferred probes according to the invention will not hybridize detectably to total female bovine DNA in an hybridization under stringent conditions over an hybridization period during which detectable hybridization with total male bovine DNA does occur.

Preferably the probes according to the invention will be employed in hybridizations under stringent conditions with total (i.e., chromosomal) DNA derived from cells of an embryo or fetus of the species being tested. Stringent conditions and total DNA are defined in more detail below.

Preferred nucleic acids and probes according to the invention, derived from bovine male DNA, are described in detail in the following examples.

As is well known in the nucleic acid hybridization probe art, nucleic acids with different sequences may, under the same conditions, hybridize detectably to the same "target" nucleic acid. Two nucleic acids hybridize detectably, under stringent conditions over a sufficiently long hybridization period, because one ("probe") comprises a segment of at least about 10 nucleotides ("probing segment") in a sequence which is complementary or nearly complementary to the sequence of at least one segment ("target segment") in the other ("target"). The physical basis for hybridization is base-pairing between these complementary or nearly complementary segments. If the time during which hybridization is allowed to occur is held constant, at a value during which, under preselected stringency conditions, two nucleic acids with exactly complementary base-pairing segments hybridize detectably to each other, increasing departures from exact complementarity can be introduced into the base-pairing segments, but base-pairing will nonetheless occur to an extent sufficient to make hybridization detectable, as the base-pairing segments of two nucleic acids become larger and as conditions of the hybridization become less stringent. Further, segments outside the probing segment(s) of a probe nucleic acid (that hybridizes to a particular target nucleic acid) can be changed completely in sequence without substantially diminishing the extent of hybridization between the probe and its target, if the change does not introduce a probing segment complementary (or nearly complementary) to a target segment in a different target present in samples to be probed. Even if no such new probing segment is introduced, if the segments outside the probing segment are changed substantially in length, the rate of hybridization might be altered. Two single-stranded nucleic acid segments have "substantially the same sequence," within the meaning of the present specification, if (a) both form a base-paired duplex with the same segment, and (b) the melting temperatures of said two duplexes in a solution of 0.5xSSPE differ by less than 10° C. If the segments being compared have the same number of bases, they will typically differ in their sequences at fewer than 1 base in 10 to have "substantially the same sequence". Two double-stranded nucleic acid segments have "substantially the same sequence" if either strand of one of the segments has "substantially the same sequence" as one strand of the other of the segments.

Methods for determining melting temperatures of nucleic acid duplexes are well known. See, e.g., Meinkoth and Wahl, Anal. Biochem. 138, 267–284 (1984) and references cited therein.

To be used as an hybridization probe in accordance with the present invention, a nucleic acid according to the invention must be rendered detectable by being labeled. Preferably the nucleic acids of the invention are detectably labeled with $^{32}P$. Other radioactive labels, such as $^3H$ or $^{14}C$, may also be employed.

Detectably labeling a DNA of the invention with a radioactive isotope is conveniently accomplished by nick-translating a sample of the DNA in the presence of one or more deoxynucleoside-5'-triphosphates which are themselves labeled with the isotope.

Non-radioactive labels known in the art can also be employed, provided they render the probes according to the invention sufficiently sensitive for sexing during the time available (for culturing cells, if necessary; extracting DNA; and hybridization assay) with DNA from the number of cells available as source of DNA. Clearly, a probe to be used to determine, within a few days, the sex of an embryo with DNA from four cells will need to be more sensitive than a probe to be used for determining, within 30 days, the sex of a fetus with DNA from $10^4$ cells.

A nucleic acid according to the invention can be made detectable by being chemically labeled. One method of chemically detectably labeling such a nucleic acid that is a DNA is to nick-translate the nucleic acid in the presence of deoxyuridylate biotinylated at the 5-position of the uracil moiety to replace thymidylate residues. The resulting probe will include the biotinylated uridylate in place of thymidylate residues and can be detected (via the biotin moieties) by any of a number of commercially available detection systems based on binding an avidin-enzyme complex or streptavidin-enzyme complex to the biotin. See Langer et al., Proc. Natl. Acad. Sci. U.S.A. 78, 6633–6637 (1981); Langer-Safer et al., Proc. Natl. Acad. Sci. U.S.A. 79, 4381–4385 (1982); Singer and Ward, Proc. Natl. Acad. Sci. U.S.A. 79, 7331–7335 (1982); Leary et al., Proc. Natl. Acad. Sci. U.S.A. 80, 4045–4049 (1983); Brigati et al., Virology 126, 32–50 (1983). The above-mentioned commercially available detection systems can be obtained from, e.g., Enzo Biochemicals, Inc., New York, New York, U.S.A. and Bethesda Research Laboratories, Inc., Gaithersburg, Maryland, U.S.A.

Making and using the nucleic acids and probes of the invention are described in detail in the following examples.

To make a nucleic acid according to the invention, a genomic library (which will usually be a partial genomic library) of the male of the species of interest is prepared, screened with a male specific DNA preparation (also referred to as "male specific probe preparation") of DNA from the male of the species to identify clones (or colonies which comprise clones) which include DNA with which DNA of the male-specific probe preparation hybridizes, and then screening the clones (or colonies) so identified for clones which include DNA which hybridizes to a greater extent with male DNA than with female DNA. Preferably the clones identified in the second screening are further screened to identify the clones containing DNA which hybridizes detectably within 20 hours with total male DNA but not total female DNA of the species in an assay conducted under stringent conditions, with the DNA of the clones labeled radioactively to a high specific activity (approximately $4 \times 10^8$ CPM/ug).

The clones identified in the screening, wherein the extent of hybridization with male DNA and female DNA is compared, harbor cloned DNA, usually in the form of plasmid or phage vectors, which are nucleic acids according to the invention. Each of these cloned DNAs, in turn, includes a segment of genomic DNA, from the male of the species of interest, which is an element of the genomic library or partial library harbored in the set of screened clones and is also a nucleic acid according to the invention.

In preparing a male genomic or partial genomic library, for screening for clones with nucleic acid of the invention, digestion of male chromosomal DNA with any one or more restriction endonucleases with a recognition sequence of four, five or six base pairs (bp), or random fragmentation of male chromosomal DNA to an average size of about 1,000 bp, by sonication or digestion with DNaseI, is suitable. For bovine male DNA, digestion with RsaI alone or both RsaI and EcoRI together are preferred. If a partial genomic library is prepared for screening, it will preferably include DNA fragments between about 100 bp and about 10,000 bp in length, more preferably 150 bp to 7,000 bp.

Any cloning vector, such as a lambda phage or cosmid vector or any of various plasmid vectors, that is suitable for preparing a genomic or partial genomic library, can be employed for making the library of male DNA. Typically such vectors will be less than about 50 kilobase pairs (kbp) in size. Plasmid pBR322, cleaved at the single PstI site, and tailed with dGTP, is conveniently employed, with dCTP-tailed chromosomal DNA fragments, as described in the examples below. Lambda-gtll, with genomic fragments, with EcoRI sticky ends or ligated to EcoRI adapters to provide such sticky ends and inserted at the EcoRI insertion side of the vector, can also be employed, also as described in the examples.

The male specific DNA preparation ("male specific probe preparation") used in various screening steps is prepared by solution hybridization of randomly fragmented, labeled total male DNA, with an average fragment size of about 10 to about 1,000, preferably about 400 to about 800, nucleotides with a 10-fold to $10^5$-fold, preferably about $10^3$-fold, mass excess of randomly fragmented total female DNA, with an average fragment size of about 10 to about 1,000, preferably about 400 to about 800, nucleotides. The hybridization is carried out for 20–30 hours, preferably about 24 hours, at stringency conditions defined by: a temperature of 37° C. to 50° C., preferably about 42° C., in 40% (v/v)-60% (v/v), preferably about 50% (v/v), deionized formamide; 0.7X to 1.3X, preferably about 1.0X, Denhardt's solution; 4X to 6X, preferably about 5X, SSPE; 7% (w/v) to 13% (w/v), preferably about 10% (w/v), dextran sulfate; and 400 ug/ml to 600 ug/ml, preferably about 500 ug/ml, heparin. The concentration of labeled male DNA is preferably about 1 ug/ml. After the solution hybridization, the DNA solution is preferably filtered through a material such as nitrocellulose. A male specific probe preparation is a solution of DNA fragments essentially all of which include at least one segment of longer than 10 nucleotides which occurs in total male, but not in total female, DNA of the involved species. DNA can be randomly fragmented by known methods, including sonication and digestion with DNaseI; and the average size of fragments can be estimated with sufficient accuracy for purposes of the present invention by standard DNA sizing techniques (e.g., comparing migration distance of fragmented DNA during electrophoresis on an agarose gel with fragments of known size). The randomly fragmented, labeled total male DNA is conveniently prepared by nick-translation of total male DNA with alpha-$^{32}$P-labeled nucleoside triphosphates, following standard nick-translation procedures, to obtain DNA fragments of the desired average size and labeled to the desired specific activity. See Maniatis et al., Molecular Cloning: A Laboratory Manual, Cold Spring Harbor Laboratory Press., Cold Spring Harbor, N.Y. (1982), pp. 109–112. The preparation of total male DNA and total female DNA is described in Example I below. A preferred nick-translation procedure is described in Example II.

The screening of genomic library with the male specific probe preparation is preferably carried out on a solid support, such as nitrocellulose, which has been prehybridized first with DNA unrelated to that of the species of interest, such as randomly fragmented herring sperm DNA, herring testes DNA, or salmon testes DNA or randomly cleaved tRNA (homochromatography mix, described by Jay et al., Nucl. Acids Res. 1, 331–354 (1974)), and then randomly fragmented, single-stranded total female DNA of the involved species, with a random fragment size of about 10 to about 1,000, preferably about 400 to about 800, nucleotides.

Optionally, prior to preparation of the genomic library, digests of male chromosomal DNA and female chromosomal DNA with one or more restriction endonucleases can be probed by Southern hybridization using the male specific probe preparation to attempt to identify digestion procedures to produce, as well as size ranges of, male DNA fragments for a partial male genomic library that is likely to contain nucleic acid according to the invention. An example of such an optional procedure is provided in Example II below. If DNA at a position in such a Southern blot of male DNA hybridizes more strongly with DNA of the male specific probe preparation than DNA at the corresponding position in the blot of female DNA hybridized with the same male specific probe preparation, then a library of male DNA of size corresponding to the position is likely to contain nucleic acid of the invention.

The second and third screening steps, to pick, from clones identified in the first screen, those that include DNA that not only hybridizes to male but hybridizes to a greater extent with male than female DNA, are carried out generally as outlined in the following examples. The second step entails generally probing DNA in two replicas of the clones that were identified in the first step as possibly containing male-specific DNA. One replica is probed with a male specific probe preparation made in essentially the same way as that used in the first screening step. The other replica is probed with a preparation of labeled, randomly fragmented female DNA, with an average fragment size approximately the same as that of the DNA in the male specific preparation and prepared conveniently by nick-translation with one or more alpha-$^{32}$P-labeled nucleoside triphosphates and otherwise in the same way as the male specific probe preparation but without solution prehybridization with female DNA. The two replicas are probed under comparable conditions so that clones with DNA that hybridizes to a greater extent with male than female DNA can be identified by simply comparing the intensity of signal from each clone on the replica hybridized with labeled male-specific probe, with the intensity of signal from the corresponding clone on the replica hybridized with labeled female-specific probe.

The third step entails screening the cloned male genomic DNA identified in the second step for ability to hybridize under stringent conditions to a significantly greater extent with total male than with total female DNA. The third step is intended to identify clones (i.e., cloned DNAs) that clearly detectably hybridize with total male DNA and do not detectably hybridize with total female DNA of the species of interest over the time period of hybridization and detection. Such clones are "male specific". They are especially useful as the basis for nucleic acid hybridization probes for prenatal sexing of embryos and fetuses of the involved mammalian species.

In a preferred procedure, the third screening step involves using nick-translated vector DNA (including insert) from each of the clones isolated in the second screening step as a probe of a Southern digest of both male and female total DNA and identifying the clones containing DNA that hybridizes detectably with the male but not the female DNA.

Application of probes of the invention to sex mammalian embryos is described in the Examples.

A method for determining whether a nucleic acid of the invention is suitable to provide probe of the invention for sexing a mammal prenatally with chromosomal DNA from fewer than a preselected number of embryonic or fetal cells is provided in Example VI below. The method comprises simply carrying out hybridizations, with probe prepared from the nucleic acid, with increasing dilutions of total male and total female DNAs and determining the smallest quantity of DNA at which hybridization with the male DNA is distinguishable from that with the female DNA when hybridization and detection are conducted over time periods deemed to be suitable (e.g., comparable to periods to be employed with the probes in commercial applications).

Generally, a nucleic acid according to the invention is labeled prior to hybridization with DNA from cells of the embryo or fetus to be sexed.

Particularly with embryo sexing, where the amount of embryonic DNA available as "target DNA" for hybridization is generally quite small, radioactive labeling of nucleic acid of the invention to high specific activity (e.g., approximately 1 to $2 \times 10^9$ CPM/ug) is preferred; a convenient method of accomplishing such labeling is nick-translation of nucleic acid of the invention with deoxynucleoside-5'-triphosphates labeled with $^{32}$P to a high specific activity (e.g., 2500–3500 Ci/mmole). The nick-translation is preferably carried out so that the average size of nick-translated product is 500–600 base pairs (bp), with a size range between about 300 bp and about 1000 bp.

It will be recognized that RNA probes according to the invention could be prepared by synthesis of $^{32}$P-labeled RNA with an in vitro synthesizing system employing alpha-$^{32}$P-labeled (ribo) nucleoside triphosphates with DNA-dependent RNA-polymerasecatalysis and DNA according to the invention as template.

The total (i.e., chromosomal) DNA is isolated from cells of the fetus or embryo to be sexed and, preferably, affixed to a solid support such as nitrocellulose. The nitrocellulose with DNA fixed is then typically prehybridized, preferably under stringent conditions, to minimize non-specific binding of probe. Then the DNA on the (prehybridized) nitrocellulose is hybridized, also preferably under stringent conditions over a period of about 17 hours, with labeled probe according to the invention. Then, after post hybridization washing, also preferably under stringent conditions, the support is treated appropriately to observe any signal associated with detectable label on probe that might have hybridized and thereby, preferably by comparison with signals from controls, ascertain whether significant hybridization between probe and fetal or embryonic DNA occurred. Procedures that may be employed in detecting signal from hybridized probe are well known in the art. For $^{32}$P-labeled probe, preferred autoradiographic procedures are provided in the examples; scintillation counting may also be employed.

As illustrated in the Examples, hybridization of labeled probe with test DNA, i.e., DNA derived from cells of an embryo or fetus being sexed, will be conducted in parallel with suitable control hybridizations, whereby the number of embryonic or fetal cells from which test DNA was derived can be estimated and signal from probe hybridization to test DNA can be compared with signal from probe hybridized to total DNA known to have been derived from a male and total DNA known to have been derived from a female of the involved species.

As the amount of test DNA falls below the amount of DNA that can be obtained from about 10 embryonic or fetal cells, the reliability of the sex determination decreases significantly. It is essential to be sure that there is embryonic DNA in the assay system at the stage in an assay at which male specific probe is hybridized with test DNA. Further, an estimate of the amount of test DNA is important in order to be able to confirm the reliability of the determination. A method is described in Example IX, using a probe which is not male-specific but does hybridize strongly to DNA of the involved species, to confirm that embryonic test DNA is present to be probed and to estimate the amount of such test DNA.

Significant hybridization of probe with DNA from an embryo or fetus indicates the embryo or fetus is a male. The absence of significant hybridization indicates the embryo or fetus is a female. Because background signal is unavoidable in hybridization assays, the presence or absence of significant hybridization is determined by comparing signals from hybridization of probe with test DNA with signals from hybridization of probe with known male DNA and known female DNA of the involved species. Significant hybridization of probe with embryonic or fetal test DNA is indicated by a signal with that DNA that is significantly above the signal from the hybridization with known female DNA, and significant hybridization is confirmed if the signal from hybridization with the embryonic or fetal test DNA is approximately the same, after adjustment for differences in amounts of DNA, as that from the hybridization with known male DNA. The absence of significant hybridization is indicated by signal with embryonic or fetal test DNA that is approximately the same as the signal with known female DNA and is confirmed by the signal with embryonic or fetal test DNA being significantly less than that with known male DNA, after adjustment for differences in amounts of DNA.

As shown in the Examples below, employing the preferred male-specific nucleic acids of the invention together, the sex of an embryo can be determined with at least 95% accuracy when at least 10 embryonic cells are available as source of test DNA.

The most preferred probes according to the invention are those which hybridize appreciably only with male DNA. With such probes, single negative control hybridization (with DNA derived from a female of the species) run in parallel with hybridization of test DNA, from the fetus or embryo being sexed, would be sufficient, for accurate sexing, provided that the amount of test DNA is sufficient so that signal from hybridization to test DNA (if male) is greater than that due to background hybridization and low level (if any) hybridization to female control DNA. With the highly labeled, combined, preferred probes of the present invention, pES5(2), pES8 and lambda-ES6.0, prepared and labeled as illustrated in the examples below, DNA from more than about 10 bovine embryonic cells is sufficient for reliable sexing when negative control is 1 ng of bovine female DNA.

As will be apparent to those of skill, once a nucleic acid of the invention that consists of double-stranded DNA is prepared, numerous techniques are available to make a corresponding single-stranded DNA (simply by strand separation), a corresponding single-stranded or double-stranded RNA, and corresponding DNA-RNA hybrids.

The sequence of a nucleic acid of the invention can be determined, using known techniques. Then, in addition to various enzymatic in vitro and in vivo methods for making large quantities of the nucleic acid, automated, in vitro, stepwise synthesis techniques for making the nucleic acid, and segments thereof, labeled as well as unlabeled, can be employed.

Those of skill will also recognize that various components necessary for carrying out prenatal sexing of a mammal in accordance with the instant invention can be assembled into kits to facilitate sexing on site at embryo-transfer companies, in veterinarians' offices, or on dairy farms, cattle ranches, and the like.

The invention is now described in greater detail in the following examples:

EXAMPLE I

The procedure for the preparation of bovine chromosomal DNA is described in this Example. DNA prepared according to this Example from male bovine tissue is also referred to in the specification as "total (bovine) male DNA" or simply "(bovine) male DNA." Similarly, DNA prepared according to the Example from bovine female tissue is also referred to as "total (bovine) female DNA" or simply "(bovine) female DNA."

Male Holstein bovine liver and female Hereford bovine liver were obtained from the Talone Packing Company, Escondido, Calif., U.S.A. The tissue from each sex was processed separately, but by the same procedure, to yield a preparation of male bovine chromosomal DNA (also referred to herein as "total male DNA") and a preparation of female bovine chromosomal DNA (also referred to herein as "total female DNA").

Liver tissue (40 g) was powdered in a Waring Blender in the presence of liquid nitrogen. The liquid nitrogen was allowed to evaporate, and the powdered tissue was then transferred to a beaker containing 400 ml of PK buffer. Immediately thereafter, proteinase K (20 mg) in 1 ml of $H_2O$ was added to the tissue/buffer mixture, which was then vigorously mixed and allowed to incubate at room temperature (20° C. to 30° C.) for 30 minutes. After the incubation, an equal volume of PCIA was added to the preparation and the entire contents were then mixed vigorously. The lower organic phase and the upper aqueous phase were then separated by centrifugation, and the organic phase was discarded. An equal volume of CIA was added to the aqueous phase and the contents were vigorously mixed. The two phases were then separated by centrifugation. The organic phase was discarded, and NaCl was added to the aqueous phase, adjusting it to 0.25 M NaCl. Two volumes of ice-cold 95% ethanol were then gently layered onto the aqueous phase. The high molecular weight chromosomal DNA that precipitates was carefully spooled on to a pipet and transferred to a centrifuge tube. TE-buffer (40 ml) was added to the centrifuge tube, and the DNA was resuspended by shaking at 42° C. for 16 hours. Ribonuclease A (RNase A) was dissolved to 10 mg/ml in 10 mM Tris.Cl (pH 7.5) and 15 mM NaCl, and the resulting solution was heated to 100° C. for 15 minutes and then allowed to cool slowly to room temperature; aliquots of this preparation (referred to herein as "heat-treated RNase A") are stored at $-20°$ C. (See Maniatis et al., supra, at page 451.) Heat-treated RNase A was added to DNA suspension at a final concentration of 50 ug RNase A/ml and the suspension was then incubated at room temperature for 30 minutes. Thereafter, the suspension was extracted with PCIA and then CIA as described above in this Example. The aqueous phase which was obtained was divided into eight tubes, each containing 30 g cesium chloride and 20 mg ethidium bromide. Each tube was adjusted to a final volume of 39.5 ml with TE-buffer. The tubes were centrifuged in a Beckman VTi-50 (Vertical Tube Rotor, maximum radius 8.66 cm) (Beckman Instruments, Inc., Fullerton, Calif. U.S.A.) at 49,000 rpm (approximately $215,000 \times g$) for 18 hours. The DNA bands, which formed in the resulting cesium chloride gradients, were collected into a single centrifuge bottle, and the ethidium bromide was removed by extracting the DNA solution four times with an equal volume of TE-saturated n-butanol. DNA was precipitated by adding two volumes of 95% ethanol and holding at $-20°$ C. overnight. The ethanol-precipitated DNA was then collected by centrifugation, resuspended in TE-buffer, and NaCl was then added to a final concentration of 0.25 M. The DNA was again ethanol precipitated and collected by centrifugation. (The DNA precipitation procedure of adjusting the NaCl concentration to 0.25 M, adding 2 volumes of 95% ethanol, holding the resulting solution at $-20°$ C. for more than 12 hours or at 70° C. for 30 minutes, and collecting the DNA by centrifugation is referred to throughout this specification as "ethanol precipitation.") The DNA was finally resuspended in TE-buffer and the concentration determined by UV absorbance at 260 nm, assuming that an O.D. of 1 corresponded to a DNA concentration of 50 ug/ml. The ratio of absorbance at 260 nm to that at 280 nm was 1.8, indicating that the DNA was not significantly contaminated. (See Maniatis et al., supra, at page 468.) Typically, 1 g of tissue yielded 1 mg of DNA.

EXAMPLE II

The establishment of hybridization conditions for the visualization of male-specific bands in Southern hybridization assays (E. Southern, J. Mol. Biol., 98, 503 (1975)) of bovine male and female DNA, the identification of male-specific bands found in such assays, a male-specific probe preparation, and a nick-translation procedure employed in many of the nick-translations described in these examples are described in this Example.

Bovine male and female DNA (10 ug each), prepared as described in Example I, were digested in separate reactions with RsaI, according to the manufacturer's instructions. The digested DNA was precipitated directly from the reaction mix by adjusting the NaCl concentration to 0.25 M and then ethanol precipitating. The precipitated DNA was collected by centrifugation and resuspended in TE-buffer. The male and female DNA samples were electrophoresed using a standard procedure in parallel lanes through a 1% TBE agarose gel. (See Maniatis et al., supra, at pp. 153–163.)

Using a standard method, the RsaI-digested fragments from each lane were transferred to a nitrocellulose filter prepared for Southern hybridization. (See Maniatis et al., supra, at pp. 383–389.) Subsequent treatment of the filter was as follows:

Prehybridization of the filter was performed in two steps: First, the filter was prehybridized with sheared herring sperm DNA and, second, the filter was prehybridized with sonicated bovine female DNA. (All procedures in this and the other Examples which involve herring sperm DNA could be carried out as well with other non-mammalian DNAs such as from herring testes or salmon testes.)

Herring sperm DNA was sheared by sonication to approximately 500 base-pairs (bp) using a Sonifier 350 (Branslon Sonic Power Co., Danbury, Conn. U.S.A.). This sheared DNA was denatured by boiling for 7 minutes and then diluted to 200 ug/ml final concentration in prehybridization buffer, which consists of 50% (v/v) deionized formamide, 5X Denhardt's solution, 5X SSPE, 0.2% (w/v) sodium dodecylsulfate (SDS), and 50 ug/ml heparin. The nitrocellulose filter with the bound male or female DNA was then placed in this prehybridization buffer and incubated at 42° C. for 5 hours. After the incubation, the filter was removed from the buffer and washed briefly in 5X SSPE.

In the second prehybridization step, the filter was prehybridized in the presence of sonicated total bovine female DNA. The bovine female DNA, prepared as described in Example I, was resuspended in TE-buffer, and sonicated in the same manner as described above for the herring sperm DNA. The bovine female DNA prehybridization buffer consisted of 50% (v/v) deionized formamide, 5X SSPE, 2X Denhardt's solution, 10% (w/v) dextran sulphate, 100 ug/ml sheared herring sperm DNA, 500 ug/ml heparin, 0.2% (w/v) SDS, and 500 ug/ml sonicated bovine female DNA. In preparing the female DNA prehybridization buffer, the formamide, sheared herring sperm DNA and sonicated bovine female DNA were combined together and placed in a boiling water bath for 5 minutes. The remaining reagents were then added to the heated mixture and then combined with the nitrocellulose filter. This prehybridization was carried out over 27 hours at 42° C.

1 ug of total male bovine DNA, prepared as in Example I, was nick-translated to a specific activity of $5 \times 10^8$ CPM/ug, with an average size of about 600 to 1000 bp in the nick-translated product, as follows:

1 ug of the male bovine DNA was mixed with 15 ul 10X nick-translation buffer, 15 ul of 10X dNTP mix, 10 ul of DNase stock, 10 ul E. coli DNA polymerase I (2 units/ul), and enough $H_2O$ to bring the solution to 100 ul. Finally, 50 ul of alpha-$^{32}$P-labeled dCTP (3.1 micromolar, labeled to 3000 Curies/mmole, in 0.01 M tricine (i.e. N-tris[hydroxymethyl]methyl glycine) buffer, pH 7.6, catalog No. NEG-013H, New England Nuclear, Inc., Boston, Mass., USA) was mixed with the solution and the resulting solution was incubated at 14° C. for 2 hours. After the two hours, the reaction was stopped by the addition of 5 ul of a solution of 0.5 M EDTA and 2.5 ul of a solution of 20% (w/v) SDS. 1 M NaOH (68.5 ul) was added to the solution to bring it to a final concentration of 0.3 M NaOH. This nick-translated DNA solution was placed in a boiling $H_2O$ bath for 3 minutes and then chromatographed on a 5 ml Sephadex G-50 column in TE-buffer to separate the nick-translated DNA from unincorporated deoxynucleoside triphosphates.

For a discussion of factors affecting nick-translations, see Maniatis et al., supra, at pp. 109–111.

The nick-translated male bovine DNA (approximately 1 ug) was combined in TE-buffer with 1 mg of sonicated female bovine DNA, average fragment size 500 bp, prepared as described above, and the combined DNAs were ethanol precipitated and resuspended in 500 ul of deionized formamide. The DNA suspension was then placed in a boiling water bath for 3 minutes, and then transferred to 65° C. for 5 minutes. The resulting DNA solution was brought to a final volume of 1 ml consisting of, in addition to the DNA, 50% (v/v) deionized formamide, 1X Denhardt's solution, 5X SSPE, 10% (w/v) dextran sulfate, and 500 ug heparin, and then placed at 42° C. for 24 hours. Following the incubation, the highly concentrated DNA solution was filtered through nitrocellulose in a Sterifil Aseptic System, 47 mm Apparatus (Millipore Corp., Bedford, Mass., U.S.A.), under the assumption that labeled, nonspecifically binding components would thereby be removed, and the filtrate was added directly to the prehybridization solution containing the prehybridized nitrocellulose filter.

The solution-prehybridization of the nick-translated male DNA generated a predominantly male-specific probe (referred to in the specification as "male specific probe preparation".) When this male-specific probe preparation was filtered through the nitrocellulose (resulting in a changed male specific probe preparation) and added to the prehybridized nitrocellulose filter, the hybridization with DNA on the filter was initiated. The concentration of nick-translated probe in the filtered solution used for hybridization was $5.0 \times 10^7$ CPM/ml (specific activity was $5.0 \times 10^8$ CPM/ug), and the hybridization was carried out at 42° C. for 48 hours. After hybridization, the filter was removed from the hybridization solution and washed in 0.2X SSPE, 0.2% (w/v) SDS briefly (to eliminate formamide from the filter) at room temperature. The filter was then washed at 65° C. for 10 minutes in the same buffer, and finally washed 2 times in 0.1X SSPE, 0.1% (w/v) SDS at 65° C. for 10 minutes each wash.

Following standard procedures, Kodak X-Omat AR x-ray film was exposed with the washed filter. (See Maniatis et al., supra, at pp. 470–471.) Exposure was for 3.5 hours with an intensifying screen.

Two male-specific bands were found, identified by their appearance in the male bovine DNA blot and the absence of corresponding bands in the female bovine DNA blot. One band, which corresponds to DNA of approximately 5 to 6 kbp (kilobase pairs), was quite strong, and appeared reproducibly when the procedures described above were repeated. The other band, which corresponds to DNA of approximately 1.6 kbp, was weak and is not observed reproducibly. The 5–6 kbp band is referred to in this specification as the "5–6 kbp RsaI fragment of bovine male DNA."

Estimates of sizes of DNA's described in the present specification were made by a standard sizing method well known in the art, e.g., by comparing the distance the DNA's of interest migrate during electrophoresis in agarose gels with migration distances under comparable conditions of DNA's liberated by HindIII-digestion of lambda phage DNA and HaeIII-digestion of PhiX174 phage DNA.

The procedures of this Example were repeated with bovine DNA digested with both EcoRI and RsaI and then again with bovine DNA digested with only EcoRI. The results showed that the 5–6 kbp RsaI fragment includes at least one EcoRI site, as an approximately 4 kbp, strongly hybridizing male-specific fragment occurred in the EcoRI-RsaI digest in place of the 5–6 kbp fragment in the RsaI digest. Under the conditions used in the procedure it was not possible to locate any male-specific bands in the digest with EcoRI alone; it can be concluded nonetheless that the approximately 4 kbp male-specific fragment identified in the EcoRI-RsaI digest is bounded by an EcoRI site and an RsaI site. This 4 kbp fragment is referred to in this specification as the "4 kbp RsaI-EcoRI fragment of bovine male DNA."

This 5–6 kbp RsaI fragment and this 4 kbp RsaI-EcoRI fragment are characterized further in examples below.

EXAMPLE III

In this Example, construction of a bovine male partial genomic libraries in pBR322 and lambda-gtll are described.

(A) pBR322

Total male bovine DNA (100 ug), prepared as described in Example I, was digested with RsaI, followed by EcoRI, according to the manufacturer's instructions. Following the digestion, the DNA was ethanol precipitated directly from the digestion solution. The digested DNA was resuspended in TE-buffer and electrophoresed in a 0.8% TBE agarose gel as described in Example II. The 2,500–6,000 bp DNA fraction was isolated by electroelution into 0.5X TBE buffer according to a standard method (see Maniatis et al., supra, at pp. 164–165) and purified by ion exchange chromatography through an Elutip-d column according to the manufacturer's instructions. The DNA was ethanol-precipitated and resuspended in 8 ul H$_2$O. Approximately 10 dCMP residues were added to each 3'-hydroxy-terminus of this population of DNA fragments in a 50 ul reaction mixture consisting of 0.0075 nmoles dCTP (alpha-$^{32}$P-labeled)(800 curies/mmole), 31.5 pmoles dCTP, 10 ul 5x terminal transferase buffer, 21 units terminal transferase, and H$_2$O to adjust to 50 ul. The reaction mixture was incubated at 37° C. for 30 minutes and then terminated by the addition of 2 ul of 0.5 M EDTA, pH 8.0. The dCMP-tailed DNA mixture was then extracted with PCIA followed by CIA as described in Example I. The aqueous phase was chromatographed through a 1.5 ml Bio Gel P.60 column in TE-buffer, to separate unincorporated deoxynucleoside triphosphates from the mixture, and the dCMP-tailed high molecular weight peak was collected in a microfuge tube. Thereafter, the volume was reduced to 50 ul by extracting with n-butanol, and the DNA was ethanol-precipitated. The dCMP-tailed DNA was then resuspended in 2.5 ul TE-buffer. The dCMP-tailed DNA was annealled to 250 ng of dGMP-tailed pBR322 in 50 ul of buffer consisting of 10 mM Tris (pH 7.4), 100 mM NaCl, and 1 mM EDTA. The reaction was carried out at 65° C. for 3 minutes, then at 42° C. for 2 hours, and finally the solution was allowed to cool slowly to room temperature.

The constructed plasmid library, thus obtained, was added to 200 ul of competent *E. coli* LE392, prepared as described below, and the bacteria were transformed by incubating the mixture on ice for 10 minutes, then at 37° C. for 5 minutes and finally on ice for 10 minutes. The transformed bacteria were then diluted with 250 ul of 2X Luria Broth (LB) and incubated at 37° C. for 45 minutes. The bacteria were plated onto 2X LB agar plates containing 15 ug/ml tetracycline and incubated at 37° C. The resulting library consisted of 4,000 colonies.

Any strain of *E. coli* suitable for cloning vectors with a ColE1 replication system, such as pBR322, could be used in place of *E. coli* LE392 in all steps described in the present specification in which *E. coli* LE392 was used. Many such strains are known and readily available to the skilled.

*E. coli* LE392 is available to the art. Its genotype is F$^-$, hsdR514(r$_K^-$ m$_K^-$), supE44, supF58, lacY1 or (lacI-Y)6, galK2, galT22, metB1, trpR55, lambda$^-$. See Maniatis et al., supra, at pp. 504; and Leder et al., Molec. Gen. Genet. 150, 53–61 (1977). It is available commercially from Promega Biotec, Madison, Wis., U.S.A. It is available from the American Type Culture Collection, Rockville, Md. U.S.A. (ATCC) under accession no. 33572 and the United States Department of Agriculture Northern Regional Research Laboratory, Peoria, Ill., U.S.A. under accession no. B-14219.

*E. coli* LE392 were made competent as follows: An overnight culture, grown in 2X LB, was diluted with 39 volumes of 2X LB and grown to an A$_{600}$ of 0.3; the volume of this resulting culture is the "original culture volume". The culture was chilled on ice for 10 minutes and the bacteria were then collected by centrifugation. The resulting bacterial pellet was resuspended with cold 0.1 M CaCl$_2$ in 0.4X the original culture volume and incubated 25 minutes on ice. The bacteria were then collected by centrifugation, and the pellet was gently resuspended with cold 0.1 M CaCl$_2$ in 0.01X the original culture volume and incubated on ice for 20 hours.

(B) Lambda-gtll

Total male bovine DNA (100 ug), prepared as described in Example I but using testes tissue in place of liver tissue, was digested with RsaI and EcoRI and the 3,000–6,000 bp fraction was isolated as described in Example III(A). The blunt-ended RsaI end was converted to an EcoRI sticky end compatible for cloning by the addition of the EcoRI adapter 5'-pAATTCATGTCTTACGGTCAAGG
    GTACAGAATGCCAGTTCCp-5'.

A 50X excess of adapter (i.e., about 0.5 ug) was ligated to 1.5–2.0 ug of the 3,000–6,000 bp DNA employing T4 DNA ligase according to a standard procedure in a 15 ul reaction mixture. (See, e.g., Maniatis et al., supra, at p 396.) After the incubation with the ligase, the ligase was inactivated by heating the reaction mixture at 72° C. for 15 minutes. The DNA was then digested with high EcoRI, according to the manufacturer's instructions, by adding to the solution EcoRI in 60 ul of a buffer suitable for EcoRI activity. After the digestion, EDTA was added to a final concentration of 20 mM and the mixture was electrophoresed through a 0.8% TBE gel to remove unligated adapter. The 3,000–6,000 bp fragments were isolated from the gel as described in Example III(A).

This genomic insert DNA was ligated into the EcoRI insertion site of lambda-gt11 following a standard procedure, as described by Huynh et al. "DNA Cloning Volume I, A Practical Approach," (D. M. Glover, ed., pp. 67–68. IRL Press 1985). The molar ratio of vector to insert was 1:4. The resulting library contained a total of $2.1 \times 10^5$ recombinants.

Lambda-gt11, and E. coli strains employed in cloning with it (e.g., E. coli Y1088, Y1089, Y1090, and LE392), are available in the art, including from the ATCC and commercial sources (e.g., Promega Biotec, Madison, Wis., U.S.A.). The ATCC accession numbers for lambda-gt11 (in lysogenic E. coli C600), E. coli Y1088, E. coli Y1089 and E. coli Y1090 are 37194, 37195, 37196 and 37197, respectively.

EXAMPLE IV

In this example, isolation of two male-specific genomic clones is described.

To probe the 4000-clone genomic library in pBR322 described in Example III (A) for male-specific clones, replica filters of the library were prepared as described in the next paragraph and then probed using the hybridization conditions defined in Example II.

The 4,000-colony library was lifted off the agar plates by placing a dry nitrocellulose filter on top of the colonies and gently peeling the filter, plus colonies, off the plate. The replica filter was made by placing a wet nitrocellulose filter onto the filter containing the colonies and gently pressing the two filters together. The filters were separated, and a third replica was made by again placing a wet nitrocellulose filter onto the original filter with colonies. After the filters were separated, they were placed on fresh 2X LB agar plates containing 15 ug/ml tetracycline. The plates containing the replicated filters were incubated at 37° C. until the colonies had regenerated. Two of the replicas were prepared for hybridization by lysing the colonies on the filters, neutralizing the filters, and baking them, as described below. The colonies on the filters were lysed by floating each filter on a 5 ml puddle of lysis buffer for 15 minutes. Each filter was then neutralized by transferring it to a 5 ml puddle of neutralizing buffer and allowing it to float for 15 minutes. The neutralization step was repeated once and the filters were then placed on absorbent paper towels and air dried for 30 minutes. The filters were then baked under vacuum in a vacuum oven at 70° C. for 2 hours.

Each of the two replica filters of the genomic library, prepared as described above, were probed under similar conditions as the Southern hybridization assay of Example II with the following modifications:

(1) The buffer with sheared herring sperm DNA, for prehybridization of filter with target DNA bound, contained a final concentration of 10% (w/v) dextran sulfate;

(2) The filters were removed from this 10% dextran sulfate-herring sperm DNA prehybridization buffer, lightly rubbed with a gloved hand while immersed in 5X SSPE to remove the cell debris, and then prehybridized with sonicated female bovine DNA as described in Example II, except that the Denhardt's solution was adjusted to 1X; and (3) 2 ug of total bovine male DNA were nick-translated, to an average size of about 600 bp and specific activity of $4.25 \times 10^8$ CPM/ug, following the procedure of Example II in a reaction volume of 300 ul, and used to make male-specific probe preparation, also as in Example II, that was then used for the hybridization.

15 positive colonies were thus identified.

From the third replica, these colonies and those near them were picked with a sterile toothpick into separate wells of a 96-well microtiter dish with each well containing 200 ul of 2X LB and 15 ug/ml tetracycline. For positive colonies closely spaced to other colonies, 8 colonies were picked and transferred to separate wells. For positive colonies well isolated from other colonies, 2 to 4 colonies were picked and transferred to separate wells. A total of 76 wells were inoculated. The microtiter dish was incubated at 37° C. until the media in the 76 wells became turbid. The bacteria in the wells were replica-plated onto nitrocellulose filters, which were placed on 2X LB agar plates containing 15 ug/ml tetracycline. Three replicas were made by placing a sterile device, with 96 metal prongs, designed to fit the microtiter dish, into the wells and then touching the device, with bacteria-containing drops of solution on 76 of the prongs, to the nitrocellulose filters. These filters, placed on the agar plates, were incubated at 37° C. until the colonies were 7 mm in diameter. The colonies on two of the filters were then prepared for hybridization as described above in this Example. One of these filters was then probed with 1 ug of nick-translated, bovine male specific probe preparation in the same manner as described above in this Example, including the steps for prehybridizing the filter. The other of these two filters was probed with nick-translated female bovine DNA as described in the next paragraph.

The hybridization of the filter with nick-translated female bovine DNA did not involve any solution hybridization between nick-translated female DNA with sonicated total bovine female DNA. The prehybridization of the filter with herring sperm DNA was as described in Example II. The filter was removed from the herring sperm DNA prehybridization and lightly rubbed with a gloved hand while immersed in 5X SSPE to remove cell debris. The filter was then prehybridized as described in Example II in the female bovine DNA prehybridization buffer with the omission of the total bovine female DNA. 1 ug of nick-translated total female DNA was prepared by the nick-translation procedure of Example II. The nick-translated female DNA was taken up in TE-buffer with 2.8 mg of sheared herring sperm DNA (average fragment size 500 bp), and the combined DNAs were ethanol precipitated and finally resuspended in 500 ul of deionized formamide. The DNA suspension was then placed in a boiling water bath for 3 minutes, and then transferred to 65° C. for 5 minutes. The resulting DNA solution was brought to a final volume of 1 ml consisting of, in addition to the DNA, 50% (v/v) deionized formamide, 1X Denhardt's solution, 5X SSPE, 10% (w/v) dextran sulfate, and 500 ug heparin. The solution was then filtered through nitrocellulose in a Sterifil Aspetic System 47 mm Apparatus (Millipore) and added directly to the bovine female DNA prehybridization buffer (including filter with DNA bound).

The post-hybridization washings and autoradiograph procedures employed with both probes were as described in Example II, except that the exposure of the filter probed with male DNA probe preparation was for 16 hours with an intensifying screen and the exposure of the filter probed with nick-translated female DNA was for 1.5 hours without an intensifying screen.

By comparing the intensities of the hybridization signals from the autoradiographs of the filters probed with male and female bovine DNA probes, respectively, 4 male-specific clones were identified.

These 4 clones were further characterized by isolating plasmid DNA and probing genomic Southern hybridization filters as described presently.

Plasmid DNA from each was isolated from 10 ml cultures following the quick boiling method described by Holmes and Quigley Anal. Biochem. 114, 193-197 (1981), (also described in Bethesda Research Laboratories, Inc.'s Focus, volume 3 No.2, page 4 (1981)), with some modifications as follows: Each clone was picked with a sterile toothpick and seeded into 10 ml of 2 X LB containing 15 ug/ml tetracycline, and the culture was grown at 37° C. for 8 hours. Then chloramphenicol was added to a final concentration of 200 ug/ml and the culture was incubated at 37° C. for an additional 14 hours. The cells were then pelleted in a centrifuge tube and then resuspended, with vortex mixing in 700 ul of STET. The resuspended cells were then transferred to a siliconized 13×100 mm disposable glass test tube. 50 ul of stock lysozyme was added and the mixture was brought rapidly to a boil by placing the tube directly into a flame. Immediately after the boiling, the cell mass was transferred to a microfuge tube and centrifuged at 12,000×g for about 10 minutes at room temperature. The supernatant was removed by pipetting into a microfuge tube and mixed with an equal volume of cold isopropanol and held at −20° C. for 15 minutes. The precipitated DNA was pelleted by centrifugation, then resuspended in 100 ul TE-buffer and finally PCIA and CIA extracted as described in Example I. The aqueous phase (95 ul) was removed to another microfuge tube, the concentration of NaCl in the solution was brought to 0.25 M and the DNA was then ethanol precipitated and finally resuspended in 10 ul of TE-buffer. 1 ul of each preparation was then nick-translated in a 15 ul nick-translation reaction mixture (Example II) to a specific activity of $3.1 \times 10^8$ CPM/ug. The nick-translated product was chromatographed on a Sephadex G-50 column in TE-buffer as described in Example II, but using a 1 ml column instead of a 5 ml column. $1 \times 10^7$ CPM were added directly to the prehybridization buffer as described below.

Male and female bovine DNA (40 ug each), prepared as described in Example I, were digested with RsaI in separate tubes according to the manufacturer's instructions. Thereafter, 10 ug of digested DNA was loaded into each well of a 1% TBE agarose gel, with the male and female DNAs loaded in alternating lanes to produce 4 sets of lanes with male and female DNA in adjacent lanes. The DNA was electrophoresed through the agarose gel and a Southern hybridization filter prepared as described in Example II. After the filter was baked, it was cut into four equal filters, each containing one male and one female RsaI-digested sample of bovine chromosomal DNA.

Each of the four filters was probed with a different one of the nick-translated probes after prehybridization, as follows:

The filter was prehybridized in 5 ml of 50% (v/v) deionized formamide, 5X SSPE, 5X Denhardt's solution, 0.1% (w/v) SDS, and 200 ug/ml sheared and boiled herring sperm DNA. This prehybridization was carried out with incubation at 42° C. for 5 hours. The hybridization was then initiated by the addition of 64.5 ul ($1 \times 10^7$ CPM total) of nick-translated plasmid probe in TE-buffer directly to the prehybridization solution (including the filter with DNA bound), yielding a final concentration of $2.0 \times 10^6$ CPM/ml. The hybridization was carried out at 42° C. for 17 hours. The conditions of temperature, pH, ionic strength and osmolality of the prehybridization step and hybridization step specified in this paragraph define "stringent conditions" for a prehybridization step and a hybridization step, respectively, as the term "stringent conditions" is used for such steps in the present specification.

As described in Example II, the filters were post-hybridization washed and exposed (for 2 hrs. 45 min. with intensifying screen) to X-Omat AR X-ray film. The conditions of temperature, pH, ionic strength and osmolality in this post-hybridization wash procedure define "stringent conditions" for post-hybridization washing, as the term "stringent conditions" is used for such washing in the present specification.

Unless it is clear from the context that the reference is to the hybridization step alone, reference in the present specification to "hybridization under stringent conditions" means prehybridization of the filter (with bound target DNA), hybridization, and post-hybridization washing under conditions, for each of the three steps, of temperature, pH, ionic strength and osmolality equivalent to "stringent conditions" for the step, as defined in the two preceding paragraphs.

The resulting autoradiographs indicate that two of the clones are male-specific. Both produced a range of positive hybridization signals from approximately 300 bp to approximately 6000 bp. There was complete absence of hybridization in the female lanes probed with either of these positive, male-specific clones. The two male-specific clones (cloned plasmids) have been designated pES5(2) and pES8.

EXAMPLE V

A preparative procedure for each plasmid, pES5(2) and pES8, and the characterization of their respective male-specific inserts, are described in this Example.

The plasmid-bearing E. coli LE392 was grown to an $A_{600}$ of 1.0 in 1X LB medium containing 15 ug/ml tetracyline. The plasmid copy number was then amplified by adding chloramphenicol to a final concentration of 200 ug/ml and incubating at 37° C. for 12 hours with vigorous shaking. The bacteria were then collected by centrifugation and washed by resuspending the bacterial pellet in ice-cold TEN buffer, and again collecting the cells by centrifugation. The bacterial pellet was then resuspended in ice-cold STE buffer. After the bacteria were resuspended, lysozyme stock was added to bring lysozyme to a concentration of 450 ug/ml. Lysis was achieved by then adding 5 M NaCl to a concentration of 2.0 M, followed by the addition of an equal volume of 0.2% (v/v) Triton X-100 and 40 mM EDTA, making a final NaCl concentration of 1.0 M, and incubation of the preparation on ice for 30 minutes. Then the preparation was centrifuged in a Sorval SS-34 rotor (Maximum radius 10.7 cm, DuPont de Nemours, Inc., Wilmington, Del., U.S.A.) at 20,000 rpm (approximately 48,000×g) for 45 minutes. The supernatant was transferred to another tube and then extracted with PCIA followed by CIA, as described in Example I, third paragraph, and the DNA in the aqueous phase ethanol precipitated in the presence of 1 M NaCl. The precipitated DNA, which includes the plasmid DNA, was resuspended in TE-buffer. As described in Example I, the DNA suspension was digested with heat-treated RNase A, PCIA and CIA extracted, and added to a centrifuge tube containing cesium chloride and ethidium bromide. The remainder of the preparative procedure is as described in Example I, except that two DNA bands form in the cesium chloride gradient formed in the 215,000×g, 18 hour centrifugation. The lower band, which is plasmid DNA, was collected into a centrifuge bottle and processed as described in Example I after the centrifugation step, with the resulting plasmid DNA finally resuspended in 400 ul of TE-buffer.

Each plasmid (3 ug) was digested with PstI according to the manufacturer's instructions and electrophoresed in a 1% TBE agarose gel as described in Example II. The DNA bands in the agarose gel were visualized by ethidium bromide staining according to a standard method, as described in Maniatis et al., supra, at page 161. The size of the insert fragments in pES5(2) and pES8 were estimated at 300 bp and 630 bp, respectively. These sizes include, of course, the (dG, dC) tails added to the fragments in order to ligate them into pBR322.

Two Southern hybridization filters, each containing 1 ug of PstI-digested pES5(2) and PstI-digested pES8 in adjacent lanes were prepared as described in Example II. One filter was probed with nick-translated pES5(2) and the other filter was probed with nick-translated pES8. These filters were probed using hybridization under stringent conditions. Under these conditions, the two inserts did not hybridize to each other.

The sequences of the bovine male-derived inserts in pES5(2) and pES8 were determined by a slight-modification of the Sanger dideoxy method, wherein Maloney murine leukemia virus reverse transcriptase was employed in place of *E. coli* DNA polymerase I (large fragment). Reaction buffer and reaction temperature were as prescribed by the manufacturer of the reverse transcriptase (Bethesda Research Laboratories, Inc.).

The sequence of the insert in pES5(2), with a number of restriction sites indicated, is as follows:

5'-CAAACTTACA CACACACACA CAAACCTGAT

DdeI
GCACAGTCGC CAGGGCACAG GGCTGAGAAC

AGCACACACA CACACCCACA CATAGACAGA

AAAACCCCTT GCACAGTCGC TAGGGCACAG

DdeI
GGCTGAGAAC GGCGCACACA CAAACACACA

MspI, HpaII
CACAAATAAA GACACACAAT CCGGTTTCAC

DdeI
AGTCGCCAGA GCACAGGGCT GAGAACAGCA

-continued

CACATACACA CACACAAACA CAAACTGGTT

GTGCAGTCAT CAGT-3'

The A that would be expected at the 5'-terminus of the sequence, because the insert was obtained from an RsaI-digest of bovine male DNA, is not present, presumably on account of some nuclease activity encountered between cleavage of male DNA with the RsaI and isolation of the pES5(2) clone.

The sequence of the insert in pES8, with a number of restriction sites indicated, is as follows:

DdeI
5'-ACAGTCGCCA GGGCACAGGG CTGAGCATGG

CACACACACA GACCAACACA CACACAAAGA

AACCAGTTTC AGAGTTGCCA GGGCAGAGGG

CTGGGAACAG CACACACACA CACACATACA

MspI, HpaII
CACACACACA CACACACACC GGTTGCACAG

AluI
TCGCCTGGGC ACAGAGCTGA AAATGGCACA

CACACACACA CACACACACA CACACACACA

DdeI
CACACACACA CACCAGTTAC ACTGTCACTA

AGGCACAGGG CTAAAAACAG CACACACACA

CACACACACA TATACACTCA CATACATACA

CACACAAACC GCTTGCACTG TCGCCAAGGC

ACATGGCTGA CAATGGCACA CACACACACA

CACACACGCA GACACACACA CACAGAGCAG

MspI, HpaII, AhaI        DdeI
TTTCACAGTC GCCGGGGCAC AGGGCTGAGA

AGAACACATA CATACACACA TACACACACA

AACTGCTTGC ACAGTCGTCA TGGCTCAAGG

CTGTGAATGG CACACACAAA CACTGACACA

CACACACACA CGAACAAACC ATTGCCCAAT

DdeI
CACCAGGGCA CAGGGCTGAG-3'

The T that would be expected at the 3'-terminus of the sequence, because the insert was obtained from an RsaI-digest of bovine male DNA, is not present, presumably on account of some nuclease activity encountered between cleavage of male DNA with the RsaI and isolation of the pES8 clone.

EXAMPLE VI

The number of bovine embryonic cells required for sex determination with both pES5(2) and pES8 together, and each plasmid separately, was estimated as follows: 60 nanograms each of male and female bovine chromosomal DNA, prepared as described in Example I, were resuspended separately in 2.4 ml TE-buffer to which were then added 240 ul of 3 N NaOH. The alkaline DNA solutions were incubated at 65° C. for one hour. Following the incubation, the solutions were adjusted to 1 M ammonium acetate by the addition of 2.64 ml of 2 M ammonium acetate. From these stock solutions, various masses of DNA (5,000, 1,000, 500, 100, 50, 25, 10, and 5 picograms) were aliquoted to separate tubes and the volume of each tube was adjusted to 3.52 ml with a solution prepared by mixing 2.4 parts of TE-buffer with 0.24 parts 3 M NaOH and 2.64 parts of 2 M ammonium acetate. Seven solutions, each of 440 ul, of each concentration of DNA from each sex were prepared. Three of the seven were used in triplicate hybridizations with pES5(2) alone, three were used in triplicate hybridizations with pES8 alone, and the last was used in a single hybridization with pES5(2) and pES8 together. The solutions were applied to nitrocellulose filters using a Manifold II Slot Blotter apparatus according to the manufacturer's instructions. Prior to the application of the DNA, the nitrocellulose filters, and the blotter paper or Whatman 3 mm chromatography paper, used with the apparatus, were soaked briefly in 1 M ammonium acetate. Following the application of DNA, the filters were removed from the Slot Blotter, air dried for 10 minutes, and baked under vacuum in a vacuum oven for 1 hour at 70° C. The filters were removed from the oven, and prehybridized, and then hybridized and post-hybridization washed according to the stringent conditions described in Example IV. The filters were hybridized for 17 hours with the following probes (at the following concentrations):

(1) pES5(2) alone ($1.5 \times 10^6$ CPM/ml);
(2) pES8 alone ($1.5 \times 10^6$ CPM/ml); and
(3) pES5(2) and pES8 together ($3.0 \times 10^6$ CPM/ml, each at $1.5 \times 10^6$ CPM/ml).

The specific activity of each probe was $4 \times 10^8$ CPM/ug Each probe was prepared by nicktranslating, by the procedure of Example II, 200 ng of plasmid (in a reaction mixture of 30 ul). The average size of nick-translated product was 600–1000 bp.

After elution from the Sephadex G-50 column, the concentration (in CPM/ml) of nick-translated probe (in TE-buffer) was measured, the probe solution was boiled for 3 minutes, and then an aliquot of the solution was added to the hybridization solution to bring the concentration of probe to the indicated concentration.

The autoradiographs resulting from hybridizing both probes together, prepared with a 24 hour film with intensifying screen, as described in Example II, show hybridization down to 25 picograms of male bovine DNA and no hybridization at any concentration studied to the female bovine DNA. 25 picograms of DNA is the amount of DNA that can be isolated from approximately 3 bovine cells. Hybridizations using the single plasmids alone detected less than 100 picograms of DNA (approximately 11 cells).

Thus, a probe including the bovine male-specific DNA of the PstI insert of pES5(2) and a probe including the bovine male-specific DNA of the PstI insert of pES8 can be used together to sex an embryo with as few as 4 of the embryo's cells while preserving the remaining cells.

EXAMPLE VII

In this example, bovine embryonic tissue is used as a substrate for sex determination with pES5(2) and pES8. The experiment described in the example was performed to establish that pES5(2) and pES8 would produce a positive hybridization signal with bovine embryonic DNA, and that the intensity of a positive signal does not vary significantly between four equal portions of the same embryo.

A total of twenty embryos were prepared for sex determination. Ten of these embryos were processed as whole embryos and the remaining ten embryos were divided into four equal quarters and processed as quarter embryos. The embryonic cells, either whole embryos or quarter embryos, (100-120 cells or 25-30 cells, respectively) were individually transferred in a volume of 5 ul to a 500 ul microfuge tube containing 20 ul PK buffer. This resulted in a total of 50 microfuge tubes, ten of which contained whole embryos and forty of which contained quarter embryos. Proteinase K (2.5 ul of a 2 mg/ml $H_2O$ stock) was added and the digestions were incubated at 22° C. for 15 minutes. The digestions were PCIA extracted as described in Example I and each aqueous phase was removed to a separate tube. PK buffer (20 ul) was added to the remaining PCIA and any residual DNA was extracted into the aqueous phase. This aqueous phase of each extraction was removed to the tube containing the aqueous phase for the first PCIA extraction, thus bringing the volume to approximately 40 ul. 3 M NaOH stock (4 ul) was then added to each aqueous solution and the tubes were then incubated at 65° C. for 1 hour in order to denature the DNA in each sample. Following the denaturation, 2 M ammonium acetate (50 ul) was added in order to neutralize each solution. The solutions were then applied to a nitrocellulose filter using a Manifold II Slot Blotter apparatus as described in Example VI. The filter was removed from the apparatus, air-dried, baked, prehybridized, and hybridized with nick-translated pES5(2) and pES8 together as described in Example VI. The filter was washed according to the stringent conditions described in Example IV.

The results of autoradiography (Example II) after a 68 hour exposure with an intensifying screen were as follows: 5 of the 10 slots containing whole embryos were strongly positive, and the remaining 5 slots containing whole embryos exhibited a complete absence of hybridization. Of the embryos divided into quarters, 6 of the 10 embryos produced a positive signal. For 5 of these 6, all four quarters gave a positive signal of approximately the same intensity. For the sixth, three of the quarters gave a positive signal of approximately the same intensity and one of the quarters did not give a positive signal. For 3 of the 4 quartered embryos that did not produce a positive signal, all four quarters did not. For the fourth, one of the quarters produced a positive signal and three did not.

The results show specific hybridization of the probes to bovine embryonic DNA with each quarter of an embryo producing a positive hybridization signal of equal intensity, thus indicating that the mass of DNA from the quarter of an embryo (approximately 25-30 cells) can be quantitatively recovered and probed for sex determination.

In the experiment described in this example, pES5(2) and pES8 were nick-translated with only one $^{32}$P-labeled deoxynucleoside triphosphate (see Example II). Those skilled in the art will understand that nick-translation of the plasmids with all four deoxynucleoside triphosphates labeled with $^{32}$P can result in a specific activity and sensitivity in the resulting probes at least about four times greater than the probes employed in the experiment. Thus, DNA from as few as about 6 embryonic cells can be probed for sex determination using the procedure of this example with pES5(2) and pES8 together, each nick-translated, with all four $^{32}$P- labeled deoxynucleoside triphosphates, to a specific activity of about $16 \times 10^{[}CPM/ug$.

EXAMPLE VIII

Isolation and characterization of the "5–14 6 kbp RsaI fragment" and "4 kbp RsaI-EcoRI fragment" of Example II are described in this Example.

A portion of the partial genomic library described in Example III(B) ($4 \times 10^4$ plaques) was plated in *E. coli* Y1088 following a standard procedure (see, e.g., Huynh et al., supra, at pp. 69–70). Nitrocellulose filter plaque replicas were prepared by a standard method. The filters were then assayed for male-specific clones according to the procedure of Example II with the following modification:

(1) Nick-translated probe was prepared with a 3,000 to 6,000 bp EcoRI/RsaI fragment population isolated as described in Example III(A).

(2) The filters were not prehybridized with sheared bovine female DNA.

(3) One set of replicas was probed with nick-translated fragments that had been prehybridized in solution with sheared bovine female DNA, and a second set of replicas was probed with nick-translated fragments that had not been prehybridized with sheared female DNA.

Plaques which displayed equivalent intensity in autoradiography after hybridization under both assay conditions were identified as possibly male-specific. Nine such potentially male-specific plaques were identified.

Phage DNA was isolated from each of the nine clones, corresponding to the nine potentially male-specific plaques, by the rapid, small-scale procedure of Benson and Taylor (Bio Techniques 1, pp. 126–127 (1984)). Any standard procedure for isolating lambda phage DNA could have been employed.

Each of the isolated phage DNA samples was then digested with EcoRI and assayed in a Southern filter hybridization assay. Duplicate filters were prepared. One of the duplicates was prehybridized with sheared female DNA, as described in Example II; the other was prehybridized in the same way but without the sheared female DNA.

The filter prehybridized with sheared female DNA was probed with nick-translated fragments that had been prepared with EcoRI/RsaI-digested 3,000–6,000 bp male DNA (i.e., a probe preparation equivalent to that used to identify the nine potentially male-specific phage plaques) and had been prehybridized in solution with sheared female DNA.

The filter not prehybridized with sheared female DNA was also probed with nick-translated fragments that had been prepared with EcoRI/RsaI-digested 3,000–6,000 bp male DNA but that had not been prehybridized with sheared female DNA.

For each of two of the nine clones, a band appeared on both filters at 2.2 kb (with approximately equal autoradiographic intensity from both filters) and at 4.0 kb (with approximately equal autoradiographic intensity from both filters). These two clones were thus identified as harboring lambda-gt11 with a male-specific, 6.2 kbp insert, which has an EcoRI site at about 4.0 kbp from one end, in its genome.

The 6.2 kbp insert in these two male-specific clones is consistent in size with the "5–6 kbp RsaI fragment" of Example II. The 4.0 kbp fragment is consistent in size with the "4 kbp RsaI-EcoRI fragment" of Example II.

One of the two clones was plaque purified by plating at high dilution and then probing as described above to insure that a single clone was isolated. The recombinant phage in the single clone was designated lambda-ES6.0.

Lambda-ES6.0 DNA was confirmed as having a male specific insert by nick-translating the phage DNA and probing, with the nick-translated DNA, filters of bovine male and female DNA in a Southern hybridization assay, as described at the end of Example IV.

The male-specific insert of the lambda-ES6.0 genome has been partially sequenced by the same modified Sanger dideoxy method that was used to sequence the smaller, male-specific-sequence-including, PstI-fragments of pES5(2) and pES8.

The partial sequence, with various restriction sites and the EcoRI adapter indicated, is as shown in FIG. 1.

In the sequence in FIG. 1, an N represents a position at which the sequence was unreadable; an asterisk followed by a segment with sequence in lower case letters indicates that the sequence of the segment is the best guess from ambiguous information from sequencing; and the double asterisk followed by a segment with sequence in lower case letters means that the sequence of the indicated segment is correct but that apparently the segment occurs in only about half of lambda-ES6.0 phage.

EXAMPLE IX

A procedure for sexing a bovine embryo with nick-translated pES5(2), pES8 and lambda-ES6.0 genome is described in this example.

An embryo is obtained and split by procedures known in the art and part of the embryo (preferably including at least 10 cells) is supplied in a siliconized 500 ul microfuge tube in approximately 50 ul of a solution of 50-parts PK buffer combined with 1 part of a solution of 20 mg proteinase K per ml H$_2$O. The volume of the mixture is checked visually and is adjusted with PK buffer to 50 ul by comparison with a 50 ul standard.

The part of the embryo that is not used in a sex-determining hybridization assay according to the present invention can be handled in any of a number of ways known in the art, including, but not limited to:

(1) destruction, if the sex is not desired;

(2) reimplantation into a recipient cow, which is the natural or a foster mother, for gestation to term;

(3) storage, as in freezing, for reimplantation at a time of choice; and (4) manipulation to obtain a number of identical embryos which can be reimplanted, or stored for later implantation, to provide multiple identical individuals.

Three organic extractions are performed on the sample, as follows:

(1) 50 ul of PCIA is added and the mixture is vortexed vigorously, followed by microfuging for approximately 2 minutes and then careful removal of the lower organic phase, which is discarded.

(2) Then the extraction in (1) is repeated.

(3) Then 50 ul of CIA is added and the mixture is vortexed vigorously, followed by microfuging for approximately 2 minutes and then careful removal of the upper aqueous phase to a fresh siliconized 500 ul microfuge tube. Again, the organic phase is discarded.

After the extraction of DNA from the embryonic cells, the DNA is analyzed in parallel with the following controls, all initially in 50 ul of TE buffer in siliconized 500 ul microfuge tubes and all DNA's obtained as described in Example I: 1 ng bovine female DNA, 1 ng, 500 pg, 250 pg, 125 pg, 100 pg, 75 pg and 50 pg bovine male DNA.

The test DNA (i.e., from embryo) and control DNA samples are analyzed as follows:

To each sample, 6 ul of freshly prepared 3 M NaOH solution is added, to bring the final NaOH concentration to about 0.3 M. The samples are then incubated at 65° C. for 30 minutes, cooled at room temperature, and microfuged briefly to return condensate to the solutions.

The Manifold II Slot-Blotter apparatus and nitrocellulose paper are prepared as follows: One sheet of nitrocellulose filter paper (BA 85) and two sheets of Whatman 3 MM chromatography paper are cut to the size of the slot-blotter. Each cut sheet is pre-wetted with 1 M ammonium acetate (pH unadjusted) and, following the manufacturer's instructions, the blotter is assembled using the pre-wetted paper and is then connected to a vacuum source.

Samples are sequentially neutralized and loaded into the slot-blotter as follows, with each sample being both neutralized and loaded separately, rather than first neutralizing all samples and then loading all of them: A sample is neutralized by being brought to a volume of about 150 ul by addition of 84 ul of 2 M ammonium acetate (pH unadjusted). Then 100 ul of 1 M ammonium acetate (pH unadjusted) is added to two adjacent slots. 15 ul (approximately 10%) of neutralized sample is added to one and 135 ul (approximately 90%) of neutralized sample is added to the other of these adjacent slots. Then 100 ul of 1 M ammonium acetate solution is added to the microfuge tube which held the sample, and this 100 ul rinse is added to the slot with 90% of the sample. Finally, the microfuge tube which held the sample is again rinsed with 100 ul of 1 M ammonium acetate solution, and this rinse is added to the slot with 10% of the sample.

After all of the samples have been loaded, the nitrocellulose is removed from the apparatus, marked for slot locations, and baked at 70° C. under vacuum for 1 hour. The filter is then cut into two portions, one containing the 90% fractions and the other containing the 10% fractions.

The filters are then probed within 24 hours, and preferably as soon as possible, after the baking.

The blots with 10% of samples are probed with a nick-translated, non-male-specific plasmid pES12. The blots with 90% of samples are probed with nick-translated pES5(2), pES8 and lambda-ES6.0 genome together, as described presently.

In the procedure described in Example II, with digestion of total DNA with either RsaI alone, EcoRI alone, or RsaI and EcoRI together, many bands were found which hybridized strongly, and to about the same extent, with both male and female DNA. One of these bands was arbitrarily selected, from the EcoRI-RsaI digest, and the DNA was dC-tailed and cloned into PstI-cleaved, dG-tailed pBR322, following procedures described in earlier examples. From the resulting clones, one was arbitrarily picked and confirmed, also following procedures described in earlier examples for isolating male specific clones, to harbor an insert which hybridizes strongly and to approximately the same extent under stringent conditions to both male bovine and female bovine DNA. This clone is designated pES12. In experiments probing under stringent conditions equal masses of male bovine DNA with nick-translated fragments of pES12 and nick-translated fragments of pES5(2), pES8 and lambda-ES6.0 genome together, as described presently, it has been found that the pES12-derived probe hybridizes to an extent approximately 100 times greater than probe derived from the combination of male-specific clones. Thus, segments, to which the bovine-specific insert in pES12 (or fragments of the insert) hybridizes under stringent conditions occur about 100 times more frequently in bovine male DNA than segments to which the bovine male-specific inserts in pES5(2), pES8 and lambda-ES6.0 genome together (or fragments of those inserts) hybridize under stringent conditions.

pES12 was employed to estimate the amount of DNA per bovine cell, by comparing signal from hybridization between nick-translated pES12 and DNA isolated from known numbers of embryonic cells, following this example, with hybridization between nick-translated pES12 and known amounts of DNA isolated as described in Example I. There is approximately 9 pg of DNA per bovine cell.

Nick-translation of pES12, pES5(2), pES8 and lambda-ES6.0 is carried out as follows:

A reaction mix is prepared by combining 2.5 ul each of alpha-$^{32}$P-labeled dATP, dCTP, dGTP and dTTP (each at 3000 Ci/mmole and as supplied by New England Nuclear Corp. in tricine buffer), 1.65 ul of 10X nick-translation buffer, 1.65 ul containing 10 uM each of unlabeled dATP, dCTP, dGTP and dTTP, 1.0 ul of *E. coli* DNA polymerase I at 1 unit/ul, and 1.5 ul of *E. coli* DNase I solution (0.015 ug/ml DNase I in 50 mM Tris-HCl (pH 7.4), 10 mM MgCl, 1 mM dithiothreitol, and 50% (v/v) glycerol). 100 ng of the DNA to be nick-translated is combined with this reaction mix and the resulting solution is incubated for 90 minutes at 13°–14° C. After the incubation, the reaction is stopped by addition of 1 ul of 20% (w/v) sodium dodecyl sulphate (SDS) and 2 ul of 0.5 M EDTA, pH 8.0. Then 8 ul of 1 N NaOH is added and the solution is placed in a boiling water bath for 3 minutes. The solution is then desalted by being passed through a 1 ml (Pasteur pipet) Sephadex G-50 fine column with TE buffer. The high molecular weight radioactive peak should be in approximately 450 ul. 1 ul is taken and counted; intensity should be about $2 \times 10^5$ to about $4 \times 10^5$ CPM/ul, with specific activity about $1.5 \times 10^9$ CPM/ug.

The size range of nick-translated fragments is determined by electrophoresing 2 ul of nick-translated DNA solution on a 1.5% TBE agarose gel, employing about 500 ng of commercially available, HaeIII-digested phiX174 DNA for sizing. After electrophoresis, the gels are stained with ethidium bromide, photographed and dried under vacuum. The dried gels are then exposed to X-ray film for about 10 minutes at −70° C. with an intensifying screen. The average size of the nick-translated product should be about 500 to about 600 bp, with a size range from about 300 bp to about 1000 bp. If the size range extends to above 2000 bp, the nick-translated DNA should be subjected again to the just described nick-translation procedure, with titration of the DNase in the reaction, by standard procedures (see, e.g., Maniatis et al., pp. 110–111), to achieve the desired size distribution in the nick-translated fragment population.

The nitrocellulose blots are then subjected to hybridization under stringent conditions as follows:

The filters are prehybridized at 42° C. for at least 5 hours in enough prehybridization buffer so that the filters are free-floating. Prehybridization buffer is 50% (v/v) deionized formamide, 5X SSPE, 5X Denhardt's solution, 0.2% (w/v) SDS and 200 ug/ml sheared herring sperm DNA.

The hybridizations are initiated by simply adding nick-translated probe-fragments to the prehybridization solution bathing the filters.

The filters with blots of 10% of samples of test and control DNAs are hybridized with nick-translated, non-male-specific probe (e.g., pES12). The solution of this nick-translated probe is placed in a boiling water bath for 3 minutes, is microfuged briefly, and is then added directly to the filters in prehybridization solution to a final concentration of $4 \times 10^6$ CPM/ml. The hybridization is carried out at 42° C. for 17 hours.

The filters with blots of 90% of samples of test and control DNAs are hybridized with nick-translated fragments from pES5(2), pES8 and lambda-ES6.0 genome together. Enough of each of the three nick-translated preparations is pooled, in a siliconized $12 \times 75$ mm polypropylene tube, so that, in the final hybridization solution, $4 \times 10^6$ CPM/ml will arise from each of the preparations; thus, there will usually be about 200 to 250 ul of each preparation in the pooled amount. To the total volume of the pooled fragment preparations is added 150 ul of a solution of 1 mg sonicated $E.\ coli$ DNA per ml of TE buffer. The volume of the pooled fragment preparations plus the 150 ul of $E.\ coli$ DNA solution is considered 1 "part." This solution, of pooled fragment and $E.\ coli$ DNA, is boiled for 3 minutes and then 2 parts (i.e., a volume twice the size) of deionized formamide and 1 part of 20X SSPE are added. The resulting solution is placed at 42° C. for 20 minutes and is then added directly to the filters in the prehybridization solution. The hybridization is carried out for 17 hours at 42° C.

After the hybridizations, the filters are washed as follows: first, briefly at room temperature in 0.2X SSPE, 0.2% (w/v) SDS; then, 15 minutes at 65° C. in 0.2X SSPE, 0.2% (w/v) SDS; and finally, twice, each for 15 minutes at 65° C, in 0.1X SSPE, 0.1% (w/v) SDS.

The filters are then exposed at $-70°$ C. for 3 days to Kodak X-Omat-AR X-ray film employing two DuPont Cronex intensifying screens.

The signals from the 10% samples using nick-translated pES12 are compared with signals from the dilution series of male DNA to estimate the mass of test DNA from the embryo being sexed. The estimate is based on 9 pg of DNA per bovine cell. Although sexing is possible with DNA from as few as 3 or 4 embryonic cells, the reliability of the sexing has been found to decrease significantly if DNA from fewer than 10 embryonic cells is tested. The accuracy of sexing an embryo by the procedure described in this example is at least 95% when DNA from at least 10 embryonic cells is used in the procedure.

Thirteen foster cows, carrying fetuses that had developed from embryos that were sexed by the procedure of this example prior to embryo transfer, were caused to abort. The aborted fetuses were sexed by visual examination and compared with the sex determined according to the example. In all thirteen cases, the sex determined anatomically from the aborted fetus was the same as the sex determined by nucleic acid probe analysis of embryonic DNA.

EXAMPLE X pES5(2) and pES8 can be used to sex a fetus or embryo of any individual of genus Bos.

Male and female bovine total DNA was prepared from the Holstein and Hereford breeds by a modification of the procedure described in Example I: 500 mg of liver tissue from each sex of each breed was homogenized separately in 500 ul of PK buffer. Proteinase K was added to the tissue/buffer solution at a final concentration of 200 ug/ml and the mixture was incubated at room temperature for 30 minutes. The DNA preparation was then PCIA extracted and then CIA extracted, and finally the DNA was ethanol precipitated from the aqueous phase. The precipitate was resuspended in 100 ul TE-buffer. Heat-treated RNase A is then added to a final concentration of 50 ug/ml. The RNase A digestion was carried out at 37° C. for 15 minutes and the resulting solution PCIA extracted and then CIA extracted and the DNA again ethanol precipitated. The DNA was resuspended in TE-buffer.

The concentration of DNA in the preparations was determined, as in Example I, by UV absorbance, and 100 ng of each of the DNA's was applied to a nitrocellulose filter using a Manifold II Slot Blotter apparatus as described in Example VI. The nitrocellulose filter was baked, prehybridized, hybridized, and washed using the stringent conditions described in Example IV. The hybridization was with nick-translated pES5(2) and pES8 together as in Example VI and the autoradiography was also carried out as described in Example VI. With both breeds, the results indicated that pES5(2) and pES8 in combination are male-specific and useful for sexing.

EXAMPLE XI

Following the procedures of Example X, male and female chromosomal DNA from swine and sheep were analyzed. The results indicate that pES5(2) and pES8 are specific for male DNA of species of genus Bos, as no hybridization was observed with any of the swine or sheep DNA.

EXAMPLE XII

The number of segments per bovine male genome which hybridize under stringent conditions with the nick-translated male-specific inserts (or fragments thereof) of pES5(2), pES8 and lambda-ES6.0 genome have been estimated. These estimates are 1300 to 5200 for pES5(2), 300 to 1200 for pES8, and 10 to 40 for lambda-ES6.0 genome.

DEFINITIONS AND DETAILS

In the following, additional information is provided on various reagents, enzymes, solutions, buffers, media, equipment and other items referred to, as well as various abbreviations used, in the present specification:

| | |
|---|---|
| Agar | Difco Laboratories |
| | Detroit, Michigan, U.S.A. |
| Agarose | Bio-Rad, Inc. |
| | Chemical Division |
| | Richmond, California, U.S.A. |
| Bacto-tryptone and | Difco Laboratories |
| Bacto-yeast extract | Detroit, Michigan, U.S.A. |
| Bio-Gel P-60 | Bio-Rad, Inc. |
| | Chemical Division |
| | Richmond, California, U.S.A. |
| Bovine Serum | Sigma Chemical Co. |
| Albumin | St. Louis, Missouri, U.S.A. |
| | Catalog No. A2153; |
| | Fraction V, powder |
| CPM | Counts per minute, as |
| | measured on a Beckman LS7800 |
| | liquid scintillation counter |

| | | | | |
|---|---|---|---|---|
| Chloramphenicol | on the $^{32}$P channel (Beckmann Instruments, Inc., Fullerton, California, U.S.A.) Sigma Chemical Co. St. Louis, Missouri, U.S.A. Catalog No. C-0378 | | Heparin | using essentially the same procedure described above for tailing DNA fragments with dCMP residues. Sigma Chemical Co. St. Louis, Missouri, U.S.A. Catalog No. H-7005 Grade 2, porcine intestinal mucosal, Na-salt |
| CIA | 96% (v/v) chloroform, 4% (v/v) isoamyl alcohol | | Herring sperm DNA | Sigma Chemical Co. St. Louis, Missouri, U.S.A. Catalog No. D-1632 Type VII, Sodium salt |
| Deionized Formamide | 50 ml formamide are mixed with 5 g of mixed-bed ion exchange resin (AG 501-X8, 20-50 mesh, catalog no. 142-6424, Bio-Rad Laboratories, Richmond, California, U.S.A.) and the mixture stirred for 30 min. at room temperature and then filtered through Whatman No. 1 filter paper. Stored at $-20°$ C. | | Herring testes DNA | Sigma Chemical Co. St. Louis, Missouri, U.S.A. Catalog No. D-6898 |
| | | | Lambda Phage and PhiX174 DNA for Sizing | New England Biolabs, Inc. Beverly, Massachusetts, U.S.A. Lambda (Hind III), catalog no. 301-2 PhiX174 (Hae III), catalog no. 302-6 |
| 50X Denhardt's Solution | 5 g Ficoll 400 (Pharmacia, Inc., Piscataway, New Jersey, USA, catalog No. 17-0400-01, average molecular weight approx. 400,000 daltons) 5 g polyvinylpyrrolidone PVP-360 (Sigma Chemical Co., St. Louis, Missouri, USA, average molecular weight approx. 360,000 daltons) 5 g bovine serum albumin; add H$_2$O to 500 ml. | | 2X LB | 10 g Bacto-tryptone 10 g Bacto-yeast extract 5 g NaCl adjusted to 1 liter with H$_2$O autoclaved |
| | | | 2X LB Agar with 15 ug/ml tetracycline | Mix 1.5% (w/v) agar with 2X LB; autoclave, when cooled to 50° C., add tetracycline solution to tetracycline concentration of 15 ug/ml; pour into plates for setting |
| Deoxynucleoside Triphosphates | Sigma Chemical Company, Inc. St. Louis, Missouri, U.S.A. | | Lysis Buffer | 1.5 M NaCl 0.5 M NaOH |
| Deoxynucleoside Triphosphates (alpha-$^{32}$P-labeled) | New England Nuclear, Inc. Boston, Massachusetts, U.S.A. | | Lysozyme Stock | Lysozyme (Sigma Chemical Co., St. Louis, Missouri, U.S.A. Catalog No. L-6876, Grade 1) at 10 mg/ml in H$_2$O. |
| Dextran Sulfate | Pharmacia, Inc. Piscataway, New Jersey, U.S.A. Catalog No. 17-0340-01 Ave. mol. wt. approximately 500,000 d Sodium salt. | | Manifold II Slot Blotter | Schleicher and Schuell, Inc. Keene, New Hampshire, U.S.A. In place of blotter paper supplied for the machine by Schleicher and Schuell, Whatman 3 MM chromatography paper can be used. |
| DNaseI | Sigma Chemical Co. St. Louis, Missouri, U.S.A. Catalog No. D4763 (type I, bovine pancreatic) | | Neutralizing Buffer | 1.5 M NaCl 0.5 M Tris-Cl (pH 7.4) |
| DNase Stock | 0.1 ug/ml of DNase I in 50 mM Tris-HCl (pH 7.4) 10 mM MgCl$_2$ 1 mM dithiothreitol 50% (v/v) glycerol | | 10X Nick-Translation Buffer | 0.5 M Tris-Cl (pH 7.2) 0.1 M MgSO$_4$ 1 mM dithiothreitol 500 ug/ml bovine serum albumin |
| 10X dNTP mix | 200 uM each of dGTP, dATP and dTTP in 20 mM Tris (pH 7.4) | | Nitrocellulose Filters | Schleicher and Schuell, Inc. Keene, New Hampshire, U.S.A. Type BA85 |
| E. coli DNA Polymerase I | New England Biolabs, Inc. Beverly, Massachusetts, U.S.A. Catalog No. 209 (supplied in 0.1M potassium phosphate buffer (pH 6.5), 1.0 mM dithiothreitol and 50% (v/v) glycerol). 5000–15,000 units/ml is the amount of enzyme required to incorporate 10 nmole of total nucleotide into acid-precipitable form in 30 min. at 37° C. | | PCIA | 50% (v/v) phenol, 48% (w/v) chloroform, 2% (v/v) isoamylalcohol |
| | | | PK Buffer | 0.14 M NaCl 0.05 M Tris (pH 8.4) 1% (w/v) SDS 0.01 M EDTA |
| | | | Proteinase K | Boehringer Mannheim Biochemicals, Inc. Indianapolis, IN, U.S.A. Catalog No. 745-723 |
| | | | Restriction Enzymes | New England Biolabs, Inc. Beverly, Massachusetts, U.S.A. |
| Elutip-d Column | An ion-exchange column for rapid purification and concentration of DNA. Schleicher and Schuell, Inc. Keene, New Hampshire, U.S.A. | | Ribonuclease A | Sigma Chemical Co. St. Louis, Missouri, U.S.A. Catalog No. R-5250 Type X-A |
| dGMP-tailed pBR322 | New England Nuclear, Inc. Boston, Massachusetts, U.S.A. The pBR322 is linearized with PstI at the single PstI site in the bla gene on the plasmid and the ends of the linearized plasmid are tailed with approximately 10 to 20 dGMP residues at each end | | Sephadex G-50 | Pharmacia, Inc. Piscataway, New Jersey, U.S.A. Catalog No. 17-0042-01 |
| | | | 20X SSPE | 3.6 M NaCl 0.16 M NaOH 0.2 M NaH$_2$PO$_4$—H$_2$O 0.02 M EDTA adjust pH to 7.0 with NaOH |

| | |
|---|---|
| STE Buffer | 25% (w/v) sucrose |
| | 50 mM Tris-Cl (pH 7.4) |
| | 20 mM EDTA |
| STET Buffer | 8% (w/v) sucrose |
| | 5% (v/v) Triton X-100 |
| | 50 mM EDTA |
| | 50 mM Tris-Cl (pH 8.0) |
| T4 DNA Ligase | New England Biolabs, Inc. |
| | Beverly, Massachusetts, U.S.A. |
| TBE agarose gel | Agarose gel prepared with |
| | agarose at a specified (w/v) |
| | percentage in 1X TBE buffer |
| 1X TBE Buffer | 0.089 M Tris |
| | 0.089 M boric acid |
| | 0.002 M EDTA |
| | pH 7.7 |
| TE-buffer | 10 mM Tris (pH 7.4) |
| | 1 mM EDTA |
| TEN buffer | 0.8% (w/v) NaCl |
| | 20 mM Tris (pH 8.0) |
| | 20 mM EDTA |
| Terminal Transferase | Ratliff Biochemicals |
| (Calf thymus) | Los Alamos, New Mexico, U.S.A; |
| | or Boehringer-Mannheim |
| | Biochemicals, Inc. |
| | Indianapolis, Indiana, U.S.A. |
| | Catalog No. 604-100. |
| 5X Terminal | 1 M KAs(CH$_3$)$_2$O$_2$ |
| Transferase Buffer | 5 mM CoCl$_2$ |
| | 10 mM beta-mercaptoethanol |
| | pH 7.2 |
| Tetracycline Solution | 15 mg crystalline |
| | tetracycline (acid form) |
| | (Sigma Chemical Co., |
| | St. Louis, Missouri, U.S.A., |
| | catalog no. T-3258) per ml |
| | methanol. |
| ug | microgram |
| ul | microliter |

DEPOSITS

Viable cultures of *E. coli* LE392 (pES5(2)) and *E. coli* LE392 (pES8) and viable samples of lambda-ES6.0 have been deposited at the ATCC under the terms of the Budapest Treaty on the International Recognition of the Deposit of Microorganisms for Purposes of Patent Procedure and the Regulations promulgated thereunder. Samples of said deposits are and will be available to industrial property offices and other parties legally entitled to receive them under said Treaty and Regulations and in accordance with the patent laws and regulations of each country and international organization in which this application is filed and each country in which a patent based on this application is granted.

The ATCC deposit number of lambda-ES6.0 is 40236.

The ATCC deposit number of *E. coli* LE392 (pES5(2)) is 53098.

The ATCC deposit number of *E. coli* LE392 (pES8) is 53099.

While the present invention has been described herein with reference to specific examples, numerous variations and modifications will be apparent to those skilled in the art. These modifications and variations are within the scope of the invention described and claimed herein.

What is claimed is:

1. A labeled or unlabeled single-stranded nucleic acid which comprises:

(a) a segment which has substantially the same sequence as that of either strand of the 6.2 kbp EcoRI fragment of the genome of lambda-ES6.0; or (b) any segment, more than 20 bp in length, of the segment of subparagraph (a) of this Claim;

provided that said single-stranded nucleic acid hybridizes to a significantly greater extent with total DNA of males of a breed of a species of genus Bos than with total DNA of females of the breed.

2. A nucleic acid according to claim 1 which, under stringent conditions, hybridizes to a significantly greater extent with total DNA of males of a breed selected from the group consisting of Hereford and Holstein than with total DNA of females of the breed.

3. A nucleic acid according to claim 2 which is DNA.

4. A DNA according to claim 3 which has substantially the same sequence as that of either strand of a DNA selected from the group consisting of the genome of lambda-ES6.0, the 6.2 kbp EcoRI fragment of the genome of lambda-ES6.0, the 4.0 kbp EcoRI fragment of the genome of lambda-ES6.0, and the 2.2 kbp EcoRI fragment of the genome of lambda-ES6.0.

5. A DNA according to claim 4 which is either strand of a DNA selected from the group consisting of the genome of lambda-ES6.0, the 6.2 kbp EcoRI fragment of the genome of lambda-ES6.0, the 4.0 kbp EcoRI fragment of the genome of lambda-ES6.0, and the 2.2 kbp ECoRI fragment of the genome of lambda-ES6.0.

6. A nucleic acid according to claim 1 which is radioactively labeled with $^3$H or $^{32}$P.

7. A nucleic acid according to claim 1 which is non-radioactively labeled with biotin.

8. A nucleic acid according to claim 2 which is radioactively labeled with $^3$H or $^{32}$P.

9. A nucleic acid according to claim 2 which is non-radioactively labeled with biotin.

10. A DNA according to claim 3 which is radioactively labeled with $^3$H or $^{32}$P.

11. A DNA according to claim 3 which is non-radioactively labeled with biotin.

12. A DNA according to claim 4 which is radioactively labeled with $^3$H or $^{32}$P.

13. A DNA according to claim 4 which is non-radioactively labeled with biotin.

14. A DNA according to claim 5 which is radioactively labeled with $^3$H or $^{32}$P.

15. A DNA according to claim 5 which is non-radioactively labeled with biotin.

16. A labeled or unlabeled single-stranded DNA which is more than 20 bp in length, which under stringent conditions hybridizes to a significantly greater extent with total DNA of males of a breed of genus Bos selected from the group consisting of Hereford and Holstein than with total DNA of females of the breed, and which is made by the process of denaturing DNA made by nick-translation of a DNA selected from the group consisting of plasmid pES5(2), plasmid pES8 and the genome of lambda-ES6.0.

17. A DNA according to claim 16 which is radioactively labeled with $^3$H or $^{32}$P.

18. A DNA according to claim 16 which is non-radioactively labeled with biotin.

19. *E. coli* LE392 (pES5(2) or *E. coli* LE392 (pES8).

20. Phage lambda-ES6.0.

21. A double-stranded DNA which has substantially the same sequence as a DNA selected from the group consisting of the genome of lambda-ES6.0, the 6.2 kbp EcoRI fragment of the genome of lambda-ES6.0, the 4.0 kbp EcoRI fragment of the genome of lambda-ES6.0, and the 2.2 kbp EcoRI fragment of the genome of lambda-ES6.0.

22. A DNA according to claim 21 which is a DNA selected from the group consisting of the genome of lambda-ES6.0, the 6.2 kbp EcoRI fragment of the genome of lambda-ES6.0, the 4.0 kbp EcoRI fragment of the genome of lambda-ES6.0, and the 2.2 kbp EcoRI fragment of the genome of lambda-ES6.0.

23. A nucleic acid according to claim 21 which is radioactively labeled with $^3$H or $^{32}$P.

24. A nucleic acid according to claim 21 which is non-radioactively labeled with biotin.

25. A nucleic acid according to claim 22 which is radioactively labeled with $^3$H or $^{32}$P.

26. A nucleic acid according to claim 22 which is non-radioactively labeled with biotin.

27. A method of sexing an embryo or fetus of a species of a genus Bos which comprises:
   (i) contacting the DNA of cells of said embryo or fetus under hybridization conditions with one or more hybridization probes, each of which is a detectably labeled, single-stranded nucleic acid which comprises:
      (a) a segment which has substantially the same sequence as that of either strand of a fragment selected from the group consisting of:
         (1) the smaller PstI fragment of plasmid pES5(2),
         (2) the smaller PstI fragment of plasmid pES8, and
         (3) the 6.2 kbp EcoRI fragment of the genome of lambda-ES6.0; or
      (b) any segment, more than 20 bp in length, of the segment of subparagraph (i)(a) of this claim;
   provided that at least one of said single-stranded nucleic acids, under the hybridization conditions, hybridizes to a significantly greater extent with total DNA of males of a breed of a species of the genus Bos than with total DNA of females of the breed; and
   (ii) ascertaining whether significant hybridization occurs between the DNA of the cells of the embryo or fetus and the hybridization probe or probes, wherein significantly greater hybridization is an indication of the presence of a male embryo or fetus.

28. A method according to claim 27 wherein each of the hybridization probes is a nucleic acid which is radioactively labeled with $^{32}$P or $^3$H and which hybridizes under stringent conditions to a significantly greater extent with total DNA of males of a breed selected from the group consisting of Hereford and Holstein than with total DNA of females of the breed.

29. A method according to claim 28 wherein each of the hybridization probes is a DNA and is obtained by denaturing DNA made by nick-translation of a DNA with a sequence which is substantially the same as that of a DNA selected from the group consisting of closed circular pES5(2), closed circular pES8, linearized pES5(2), linearized pES8, the smaller PstI fragment of pES5(2), the smaller PstI fragment of pES8, the genome of lambda-ES6.0, the 6.2 kbp EcoRI fragment of the genome of lambda-ES6.0, the 4.0 kbp EcoRI fragment of the genome of lambda-ES6.0, and the 2.2 kbp EcoRI fragment of the genome of lambda-ES6.0.

30. A method according to claim 29 wherein each of the hybridization probes is obtained by denaturing DNA made by nick-translation, with one or more of the $^{32}$P-labeled deoxynucleoside triphosphates, of a DNA selected from the group consisting of plasmid pES5(2), plasmid pES8 and the genome of lambda-ES6.0.

31. A method according to claim 30 wherein the DNA probed is derived from at least 4 embryonic cells, the hybridization probes are a mixture of fragments obtained by nick-translation of pES5(2), pES8, and the genome of lambda-ES6.0 with all four deoxynucleoside triphosphates labeled with $^{32}$P, and the radioactively of probes derived from each of pES5(2), pES8 and the genome of lambda-ES6.0 is at least one fifth and no more than one half of the radioactivity of the mixture.

32. A method according to claim 31 wherein the DNA probed is derived from at least 10 embryonic cells.

33. A method according to claim 27 wherein one or more of the hybridization probes is a nucleic acid which is non-radioactively labeled with biotin and wherein each of the probes is a nucleic acid which hybridizes under stringent conditions to a significantly greater extent with total DNA of males of a breed selected from the group consisting of Hereford and Holstein than with total DNA of females of the breed.

* * * * *

UNITED STATES PATENT AND TRADEMARK OFFICE
CERTIFICATE OF CORRECTION

PATENT NO. : 4,960,690

DATED : October 2, 1990

INVENTOR(S) : Ellis, et al

It is certified that error appears in the above-identified patent and that said Letters Patent is hereby corrected as shown below:

Column 14, line 34: Change "$(r_k - m_k -)$" to --$(r_k\ m_k)$--.

Column 23, line 2: Change "$16 \times 10^{[}CPM/ug$" to --$16 \times 10^8 CPM/ug$--.

Column 23, line 5-6: Change "514 6 kbp RsaI fragment" to --5-6 kbp RsaI fragment--.

Column 26, line 30: Change "$MgCl$" to --$MgCl_2$--.

Column 32, line 60: Change "(2)" to --(2)--.
(Claim 19)

Column 34, line 31; Change "radioactively" to
(Claim 31) --radioactivity--.

Signed and Sealed this

Ninth Day of November, 1993

Attest:

BRUCE LEHMAN

*Attesting Officer*     *Commissioner of Patents and Trademarks*